United States Patent
Provins et al.

(10) Patent No.: US 11,591,643 B2
(45) Date of Patent: Feb. 28, 2023

(54) IN OR RELATING TO UNCLEIC ACID AMPLIFICATION PROCESSES

(71) Applicant: LumiraDx UK Ltd., London (GB)

(72) Inventors: Jarrod Provins, London (GB); Daiwei Shen, London (GB); Bryan Kraynack, London (GB)

(73) Assignee: LumiraDx UK Ltd., London (GB)

( * ) Notice: Subject to any disclaimer, the term of this patent is extended or adjusted under 35 U.S.C. 154(b) by 246 days.

(21) Appl. No.: 16/313,750

(22) PCT Filed: Jun. 30, 2017

(86) PCT No.: PCT/GB2017/051927
§ 371 (c)(1),
(2) Date: Dec. 27, 2018

(87) PCT Pub. No.: WO2018/002649
PCT Pub. Date: Jan. 4, 2018

(65) Prior Publication Data
US 2019/0226015 A1 Jul. 25, 2019

(30) Foreign Application Priority Data
Jun. 30, 2016 (GB) .................................. 1611469

(51) Int. Cl.
*C12Q 1/6844* (2018.01)
*C12Q 1/6848* (2018.01)
*C12Q 1/6853* (2018.01)
*B01L 7/00* (2006.01)

(52) U.S. Cl.
CPC ............. *C12Q 1/6844* (2013.01); *B01L 7/52* (2013.01); *C12Q 1/6848* (2013.01); *C12Q 1/6853* (2013.01); *C12Q 2521/101* (2013.01); *C12Q 2521/107* (2013.01); *C12Q 2521/307* (2013.01); *C12Q 2521/531* (2013.01); *C12Q 2525/113* (2013.01); *C12Q 2525/131* (2013.01); *C12Q 2525/301* (2013.01); *C12Q 2527/101* (2013.01); *C12Q 2537/137* (2013.01)

(58) Field of Classification Search
CPC .. C12Q 1/6844; C12Q 1/6848; C12Q 1/6853; C12Q 2521/307; C12Q 2525/131; C12Q 2527/101; C12Q 2537/137
See application file for complete search history.

(56) References Cited

U.S. PATENT DOCUMENTS

| 6,191,267 | B1 | 2/2001 | Kong et al. | |
|---|---|---|---|---|
| 6,794,142 | B2 | 9/2004 | Laird et al. | |
| 8,143,006 | B2 | 3/2012 | Kutyavin | 435/6.12 |
| 8,313,932 | B2 | 11/2012 | Moser et al. | |
| 8,822,154 | B2 * | 9/2014 | Orpana | C12Q 1/6883 435/6.12 |
| 9,428,781 | B2 | 8/2016 | Cai et al. | |
| 9,670,531 | B2 | 6/2017 | Caplin | |
| 9,689,031 | B2 | 6/2017 | Maples et al. | |
| 9,845,495 | B2 | 12/2017 | Komiya | |
| 10,036,077 | B2 | 7/2018 | Komiya et al. | |
| 10,208,333 | B2 | 2/2019 | Komiya et al. | |
| 10,316,358 | B2 | 6/2019 | Cai et al. | |
| 10,329,601 | B2 | 6/2019 | Shen et al. | |
| 10,604,790 | B2 | 3/2020 | Komori et al. | |
| 10,927,393 | B2 | 2/2021 | Zhang et al. | |
| 11,293,058 | B2 | 4/2022 | Cai et al. | |
| 11,390,909 | B2 | 7/2022 | Lamble et al. | |
| 2002/0025555 | A1* | 2/2002 | Au-Young | C07K 14/7158 435/69.1 |
| 2002/0155573 | A1* | 10/2002 | Lanes | C12Y 302/02027 435/200 |
| 2003/0082590 | A1 | 5/2003 | Van Ness et al. | |
| 2003/0211506 | A1 | 11/2003 | Kong et al. | |
| 2005/0112631 | A1 | 5/2005 | Piepenburg et al. | |
| 2006/0063175 | A1 | 3/2006 | Xu et al. | |
| 2007/0231798 | A1 | 10/2007 | Collins | |
| 2009/0017453 | A1 | 1/2009 | Maples et al. | |
| 2009/0047678 | A1* | 2/2009 | Kutyavin | C12P 19/34 435/6.12 |
| 2009/0092967 | A1 | 4/2009 | Yao et al. | |
| 2009/0299047 | A1 | 12/2009 | Korfhage et al. | 536/25.4 |
| 2011/0165575 | A1 | 7/2011 | Orpana | 435/6.12 |

(Continued)

FOREIGN PATENT DOCUMENTS

EP 2699698 A2 2/2014
JP 2004526432 A 9/2004

(Continued)

OTHER PUBLICATIONS

Joneja, A. and Huang, X. Linear nicking endonuclease-mediated strand-displacement DNA amplification. Analytical Biochemistry 2011; 414: 58-69. (Year: 2011).*

Ehses et al. Optimization and design of oligonucleotide setup for strand displacement amplification. Journal of Biochemical and Biophysical Methods 2005; 63: 170-186 (Year: 2005).*

(Continued)

*Primary Examiner* — Angela M. Bertagna

(74) *Attorney, Agent, or Firm* — Goodwin Procter LLP

(57) ABSTRACT

Disclosed is a method of performing a non-isothermal nucleic acid amplification reaction, wherein the temperature at which the method is performed is non-isothermal and subject to a reduction of at least 2° C. during amplification process steps. The present invention provides an improved nucleic acid amplification technique having one or more advantages over existing techniques including, for example, decreased reaction time, increased yield, and decreased non-specific amplification products.

29 Claims, 27 Drawing Sheets

Specification includes a Sequence Listing.

(56) References Cited

U.S. PATENT DOCUMENTS

| | | | |
|---|---|---|---|
| 2012/0077252 A1* | 3/2012 | Picataggio | C12Y 602/01003 |
| | | | 435/254.22 |
| 2012/0208192 A1* | 8/2012 | Lee | C12Q 1/686 |
| | | | 435/6.11 |
| 2015/0104788 A1* | 4/2015 | Shaffer | C12Q 1/6848 |
| | | | 435/6.11 |
| 2017/0183714 A1 | 6/2017 | Shen et al. | |
| 2019/0194747 A1 | 6/2019 | Zhang et al. | |
| 2020/0002756 A1 | 1/2020 | Lamble et al. | |
| 2021/0246487 A1 | 8/2021 | Lamble et al. | |
| 2021/0292826 A1 | 9/2021 | Shen et al. | |

FOREIGN PATENT DOCUMENTS

| | | | |
|---|---|---|---|
| JP | 2008-520232 A | 6/2008 | |
| JP | 2014513534 A | 6/2014 | |
| JP | 2015-512654 A | 4/2015 | |
| JP | 2015518735 A | 7/2015 | |
| RU | 2 260 055 | 9/1999 | |
| SU | 2 017 821 | 10/1990 | |
| WO | WO-94/23055 A1 | 10/1994 | |
| WO | WO-99/037805 A1 | 7/1999 | |
| WO | WO-01/26583 A1 | 4/2001 | |
| WO | WO-03/048393 A1 | 6/2003 | |
| WO | WO 2005/118144 A1 | 12/2005 | |
| WO | WO 2005/118853 A2 | 12/2005 | |
| WO | WO-2006/054172 A1 | 5/2006 | |
| WO | WO-2007/028833 A2 | 3/2007 | |
| WO | WO 2009/138564 A1 | 11/2009 | |
| WO | WO-2009/138564 A1 | 11/2009 | |
| WO | WO 2011/030145 A1 | 3/2011 | |
| WO | WO-2011/030145 A1 | 3/2011 | |
| WO | WO-2011/038197 A1 | 3/2011 | |
| WO | WO-2012/083189 A2 | 6/2012 | |
| WO | WO-2013/155056 A1 | 10/2013 | |
| WO | WO-2017027835 A1 | 2/2017 | |
| WO | WO-2018002649 A1 | 1/2018 | |

OTHER PUBLICATIONS

Vaughn, P. and McCarthy, T.V. A novel process for mutation detection using uracil DNA-glycosylase. Nucleic Acids Research 1998; 26: 810-815 (Year: 1998).*

Cheung, V.G. and Nelson, S.F. Whole genome amplification using a degenerate oligonucleotide primer allows hundreds of genotypes to be performed on less than one nanogram of genomic DNA. Proceedings of the National Academy of Sciences, USA 1996: 93: 14676-14679 (Year: 1996).*

Wang et al. Two Methods for Increased Specificity and Sensitivity in Loop-Mediated Isothermal Amplification. Molecules 2015; 20: 6048-6059 (Year: 2015).*

New England Biolabs. The Effect of Various Temperatures on Nicking Endonucleases. Available at https://www.neb.com/tools-and-resources/selection-charts/effect-of-various-temperatures-on-nicking-endonucleases. Accessed on Feb. 10, 2021. (Year: No Date).*

Roux, K.H. Optimization and Troubleshooting in PCR. Cold Spring Harbor Protocols 2009; doi: 10.1101/pdb.ip66 (Year: 2009).*

Roux, K.H. Single-Step PCR Optimization Using Touchdown and Stepdown PCR Programming. Methods in Molecular Biology 2002; 192: 31-36 (Year: 2002).*

Korbie, D.J. & Mattick, J.S. Touchdown PCR for Increased Specificity and Sensitivity in PCR Amplification. Nature Protocols 2008; 3: 1452-1456 (Year: 2008).*

International Search Report dated Sep. 12, 2017, issued to International Application No. PCT/GB2017/051927.

Written Opinion of the International Searching Authority dated Jan. 4, 2018, issued to International Application No. PCT/GB2017/051927.

Russian Office Action dated Nov. 30, 2020, to Russian Application No. 2019101504/04.

Aric Joneja et al., Linear nicking endonuclease-mediated strand displacement DNA amplification, NIH Public Access, Anal Biochem., Jul. 1, 2011; 414(1): 58-69.

Xin-zhuan Su et al., Reduced extension temperatures required for PCR amplification of extremely A+T-rich DNA, Nucleic Acids Research, 1996, vol. 24, No. 8.

Decision to Grant a Patent for Invention dated Sep. 24, 2021, issued by the Federal Service for Intellectual Property in corresponding application RU 2019101504/10(002569).

Notice of Opposition dated Jul. 7, 2021 issued by the European Patent Office in connection with European Patent No. EP3478853.

Google Definition—"Subject", https://www.bing.com/search?q=subject&form=SWAUA2, undated, 1 page.

"Enzymatics Product Specifications P7140-HC-L Rev C", http://www.enzymatics.com/wp-content/uploads/2014/12/P7140-HC-L-REV-C-Manta-1.0-DNA-Polymerase-PSF-EFF-May 8, 2014.pdf, May 8, 2014, 2 pages.

"Molecular Beacon Design" Public Health Research Institute, New Jersey Medical School—Rutgers, The State of University of New Jersey, https://web.archive.org/web/20160327223139/http://molecular-beacons.org/MB_SC_design.html; Mar. 27, 2016.

Alexandrov et al., 2012 Nucl. Acids Res. 40(20):10116-23.

Barnes (1994) Proc. Natl. Acad. Sci. USA 91: 2216-2220.

Baskaran (1996) Genome Res. 6: 633-638.

Caballero et al. (1997) Journal of Clinical Microbiology 35(12): 3192-3197.

Compton (1991) Nature 350, 91-92.

Eggerding (1995) Genome Res. 4: 337-345.

Frackman (1998) Promega Notes 65: 27.

Gao et al. "Rapid isothermal detection assay: a probe amplification method for the detection of nucleic acids" Diagnostic Microbiology and Infectious Disease 60 (2008) 133-141.

Henke (1997) Nucleic Acids Research 25(19): 3957-3958.

Hutton (1975) Biochem. and Biophys. Research Comm. 66(3): 942-948.

J. R. Buser et al. "Precision chemical heating for diagnostic devices", Lab Chip, 2015, pp. 4423-4432.

Jeffrey Van Ness et al. "Isothermal reactions for the amplification of oligonucleotides", Proceedings of the National Academy of Sciences, Apr. 15, 2003, pp. 4504-4509.

Jensen (2010) PLosOne 5(6): 1-5.

Kim & Smithies (1988) Nucleic Acids Research 16(18): 8887-8903.

Kurn et al. (2005) Clin. Chem. 51, 1973-81.

Lakobashvili (1999) Nucleic Acid Research 27(6): 1566-1568.

Liu et al. (1998) BioTechniques 25:1022-1028.

Lizardi et al. 1998 Nature Genetics 19, 225-232.

Masny et al. (2003) Nucleic Acids Research 31(18): e114.

Mecklenburg (1996) Advances in Molecular and Cell Biology vol. 15, Abstract only.

Nagamine et al. "Isolation of Single-Stranded DNA from Loop-Mediated Isothermal Amplification Products" Biochemical and Biophysical Research Communications 290, 1195-1198 (2002).

Notomi et al. (2000) Nucl. Acids Res. 28(12):e63.

Piepenberg et al., (2006) PLoS Biology 4(7):e204.

Sarkar (1990) Nucleic Acid Research 18(24): 7465.

Shi et al. "Nicking endonuclease-mediated isothermal exponential amplification for doublestranded DNA detection" Sensors and Actuators B: Chemical, 2016, 221-225.

Shuchard et al. (1993) BioTechniques 14(3):390-394.

Varadaraj (1994) Gene 140: 1-5.

Vincent et al. (2004) EMBO Rep. 5, 795-800.

Von Hippel et al. (2013) Biopolymers 99(12):923-54.

Walker et al. (1992) Nucl. Acids Res. 20:1691-6.

Wang et al. (2018) "Technical aspects of nicking enzyme assisted amplification" Analyst, 143, 1444.

Weighardt (1993) PCR methods and Applications, Cold Spring Harbor Laboratory Press 3(1): 77-81.

Xu et al. "Real-time quantitative nicking endonuclease-mediated isothermal amplification with small molecular beacons" Analyst, 2016, 141: 2542.

Zhang et al. (2009) Analytical Biochemistry 387(1), Abstract only.

Examination Report issued in counterpart application AU2017287852 dated Aug. 30, 2022, 6 pages.

(56) References Cited

OTHER PUBLICATIONS

Wang DG, et al. (2015) Two methods for increased specificity and sensitivity in loop-mediated isothermal amplification. Molecules. 20(4):6048-59.

Zheleznaya et al. (2009) "Nicking Endonucleases" Biochemistry (Moscow) 74(13):1457-1466.

Han et al. "Molecular Beacons: A Novel Optical Diagnostic Tool" Arch. Immunol. Ther. Exp. 61:139-48 (2013).

* cited by examiner

IN OR RELATING TO UNCLEIC ACID AMPLIFICATION PROCESSES

CROSS-REFERENCE TO RELATED APPLICATIONS

This application is a national stage of International Application No. PCT/GB2017/051927, filed Jun. 30, 2017, which claims the benefit of priority to United Kingdom Application No. 1611469.6, filed Jun. 30, 2016, in the European Patent Office, the disclosures of which are incorporated herein in their entireties by reference.

SEQUENCE LISTING

The instant application contains a Sequence Listing which has been submitted electronically in ASCII format and is hereby incorporated by reference in its entirety. Said ASCII copy, created on May 18, 2021, is named SQL.txt and is 1,389 bytes in size.

FIELD OF THE INVENTION

The present invention relates to a method of amplifying a nucleic acid, and apparatus for performing the method.

BACKGROUND OF THE INVENTION

The polymerase chain reaction (PCR) was the first widely-used in vitro method for the amplification of DNA. Although extremely powerful, the technique requires the use of thermal cycling apparatus to subject the reaction mixture to periodic temperature changes in order to effect amplification. Accordingly PCR is not especially suitable for use outside a laboratory setting, for example in the context of a point-of-care ("PoC") diagnostic device.

Partly to overcome this disadvantage, numerous different isothermal amplification techniques were devised, which avoided the need for thermal cycling. Such techniques include, for example: signal mediated amplification of RNA technology ("SMART"; WO 99/037805); nucleic acid sequence based amplification ("NASBA" Compton 1991 Nature 350, 91-92); rolling circle amplification ("RCA" e.g. see Lizardi et al., 1998 Nature Genetics 19, 225-232); loop-mediated amplification ("LAMP" see Notomi et al., 2000 Nucl. Acids Res. 28, (12) e63); recombinase polymerase amplification ("RPA" see Piepenberg et al., 2006 PLoS Biology 4 (7) e204); strand displacement amplification ("SDA"); helicase-dependent amplification ("HDA" Vincent et al., 2004 EMBO Rep. 5, 795-800): transcription mediated amplification ("TMA"), single primer isothermal amplification ("SPIA" see Kurn et al., 2005 Clinical Chemistry 51, 1973-81); self-sustained sequence replication ("3SR"); and nicking enzyme amplification reaction ("NEAR").

SDA is a technique (disclosed by Walker et al., 1992 Nucl. Acids Res. 20, 1691-1696) which involves the use of a pair of short "bumper" primers upstream to a pair of primers comprising a target-complementary portion and, 5' of the target-complementary portion, a recognition and cutting site for an endonuclease. The "bumper" primers help to initiate the SDA reaction by generating complementary single stranded target for primer amplification. The primers hybridise to respective complementary single stranded target molecules. The 3' end of the target strands are extended using a reaction mix including a DNA polymerase and at least one modified nucleotide triphosphate, using the primer as template (and likewise, the 3' ends of the primers are extended using the target as template).

The extension of the target strands generates a double stranded recognition site for the endonuclease. However, because the target is extended using a modified triphosphate, the endonuclease does not cleave both strands but instead makes a single stranded nick in the primer. The 3' ends at the nicks are then extended by the DNA polymerase (typically Klenow fragment of DNA polymerase I, which lacks an exonuclease activity). As the nicked primers are extended, they displace the initially-produced extension product. The displaced product is then free to hybridise to the opposite primer, since it essentially replicates the sequence of the target for the opposite primer. In this way, exponential amplification of both strands of the target sequence is achieved.

The amplification stage of the SDA process is essentially isothermal—typically performed at 37° C. —the optimum temperature for the endonuclease and the polymerase. However, before reaching the amplification stage it is necessary to completely dissociate the double stranded target into its constituent single strands, in order to allow the pair of primers to hybridise to their complementary target strands.

This dissociation, or "melting" is normally accomplished by heating the double stranded target to a high temperature—usually about 90° C.—in order to break the hydrogen bonds between the two strands of the target. The reaction mix is then cooled to allow the addition of the enzymes which are necessary for the amplification reaction. Because of the high temperature used to generate the single stranded targets, the SDA technique is not ideally suited to a PoC context.

U.S. Pat. No. 6,191,267 discloses the cloning and expression of N.BstNBI nicking enzyme and its use in SDA, in place of restriction endonucleases and modified triphosphates.

Another amplification technique, which is similar to SDA, is Nicking Enzyme Amplification Reaction (or "NEAR").

In 'NEAR' (e.g. as disclosed in US2009/0017453 and EP 2,181,196), forward and reverse primers (referred to in US 2009/0017453 and EP 2,181,196 as "templates") hybridise to respective strands of a double stranded target and are extended. Further copies of the forward and reverse primers (present in excess) hybridise to the extension product of the opposite primer and are themselves extended, creating an "amplification duplex". Each amplification duplex so formed comprises a nicking site towards the 5' end of each strand, which is nicked by a nicking enzyme, allowing the synthesis of further extension products. The previously synthesised extension products can meanwhile hybridise with further copies of the complementary primers, causing the primers to be extended and thereby creating further copies of the "amplification duplex". In this way, exponential amplification can be achieved.

NEAR differs from SDA, in particular, in that no "bumper" primers and initial thermal dissociation step is required. The initial primer/target hybridisation event needed to trigger the amplification process takes place whilst the target is still substantially double stranded: it is thought that the initial primer/target hybridisation takes advantage of localised dissociation of the target strands—a phenomenon known as "breathing" (see Alexandrov et al., 2012 Nucl. Acids Res. and review by Von Hippel et al., 2013 Biopolymers 99 (12), 923-954). Breathing is the localised and transient loosening of the base pairing between strands of DNA. The melting temperature (Tm) of the initial primer/target heteroduplex is typically much lower than the reaction temperature, so the tendency is for the primer to dissociate, but transient hybridisation lasts long enough for the polymerase to extend the primer, which increases the Tm of the heteroduplex, and stabilises it.

The amplification stage in NEAR is performed isothermally, at a constant temperature. Indeed, it is conventional to perform both the initial target/primer hybridisation, and the subsequent amplification rounds, at the same constant temperature, usually in the range 54 to 56° C.

Avoiding the need for thermal cycling means that isothermal techniques are potentially more useful than PCR in PoC contexts. In addition, synthesis of significant amounts of amplification product, even when starting from a very low copy number of target molecules (e.g. as few as 10 double stranded target molecules), can be achieved.

WO 2011/030145 (Enigma Diagnostics Limited) discloses an "isothermal" nucleic acid amplification reaction performed under conditions of a temperature oscillation, in which a reaction is performed initially at a predetermined temperature, the temperature is allowed to deviate up or down from the predetermined temperature, and then causing the temperature to return to the predetermined temperature at least once during the amplification reaction. More typically the temperature is allowed to "wobble" by a small amount (about 5° C.) up and down from the predetermined temperature.

The present invention aims to provide, inter alia, an improved nucleic acid amplification technique having one or more advantages over existing techniques including, for example, decreased reaction time, and/or increased yield and/or decreased non-specific amplification products.

SUMMARY OF THE INVENTION

In a first aspect, the invention provides a method of performing a non-isothermal nucleic acid amplification reaction, the method comprising the steps of:
  (a) mixing a target sequence with one or more complementary single stranded primers in conditions which permit a hybridisation event in which the primers hybridise to the target, which hybridisation event, directly or indirectly, leads to the formation of a duplex structure comprising two nicking sites disposed at or near opposite ends of the duplex; and performing an amplification process by;
  (b) causing a nick at each of said nicking sites in the strands of the duplex
  (c) using a polymerase to extend the nicked strands so as to form newly synthesised nucleic acid, which extension with the polymerase recreates said nicking sites;
  (d) repeating steps (b) and (c) as desired so as to cause the production of multiple copies of the newly synthesised nucleic acid;
  characterised in that the temperature at which the method is performed is non-isothermal, and subject to a reduction of at least 2° C., preferably at least 5° C., during the amplification process of steps (b)-(d).

In a second aspect, the invention provides apparatus for performing the method of the first aspect of the invention, the apparatus comprising temperature regulation means and programmable control means, the programmable control means being programmed to operate the temperature regulation means to perform a temperature reduction of at least 2° C., preferably at least 5° C., during the amplification process of a reaction mixture used to perform the method of the first aspect.

The amplification process of the method of the invention may be applied to generally known and conventional amplification techniques including SDA and NEAR.

Thus, for example, the amplification process may be based on the amplification process employed in strand displacement amplification, or based on that used in NEAR or indeed any other nucleic acid amplification process which relies on the creation of a single stranded nick and subsequent extension from the 3' end of the nicked strand. Accordingly the teachings of the prior art in relation to the amplification stages of SDA or NEAR will, in general, be equally applicable to the amplification process of the method of the present invention (other than the teachings of the prior art in relation to maintenance of constant temperature during the amplification).

Preferably step (a) comprises mixing a sample containing double stranded target with two single stranded primers, one of said primers being complementary to a first strand of the target, and the other of said primers being complementary to a second strand of the target, such that the two primers hybridise to the target and the free 3' ends of said primers face towards one another.

The two primers may conveniently be described as 'forward' and 'reverse' primers.

Desirably both the forward and reverse primers will comprise the sequence of a nicking enzyme recognition site. Typically the nick created by a nicking enzyme will be just outside and typically 3' of the nicking enzyme recognition site.

In a preferred embodiment, the forward primer will comprise a portion at or near its 3' end which is complementary to, and can hybridise with, the 3' end of the target sequence antisense strand, whilst the reverse primer comprises a portion at or near its 3' end which is complementary to, and can hybridise with, the 3' end of the target sequence sense strand.

In this way, a nicking enzyme recognition site is introduced at opposite ends of the target sequence, and amplification of the target sequence (together with any intervening sequence of the primers downstream of the nick site) is accomplished by performing multiple cycles of polymerase extension of the forward and reverse primers so as to form a double stranded nick site, and by nicking of the nick sites with a nicking enzyme, allowing further extension of the nicked primers by a polymerase etc., essentially as disclosed in, for example, US 2009/0017453, the content of which is herein incorporated by reference.

DETAILED DESCRIPTION OF THE INVENTION

The present invention relates to, inter alia, a method for the amplification of a selected target nucleic acid.

The target may be single stranded, double stranded, or comprise a mixture of the two. The target may comprise RNA, DNA or a mixture of the two. In particular the target might incorporate one or more modified nucleotide triphosphates (i.e. a nucleotide triphosphate not normally found in naturally occurring nucleic acids), although this is not essential and indeed not preferred.

The target may be selected from the following non-exhaustive list: genomic nucleic acid (which term encompasses the genomic nucleic acid of any animal, plant, fungus, bacterium or virus), plasmid DNA, mitochondrial DNA, cDNA, mRNA, rRNA, tRNA, or a synthetic oligonucleotide or other nucleic acid molecule.

In particular, the method may additionally comprise an initial reverse transcription step. For example, RNA (e.g. viral genomic RNA, or cellular mRNA, or RNA from some other source) may be used to synthesise DNA or cDNA using a reverse transcriptase by methods well-known to those skilled in the art. The DNA may then be used as a target sequence in the method of the invention. The original RNA will typically be degraded by the ribonuclease activity of reverse transcriptase, but if desired additional RNAse H may be added after reverse transcription has been completed. RNA molecules are often present in samples at greater copy number than corresponding (e.g. genomic) DNA sequences, hence it may be convenient to make DNA transcripts from the RNA molecule in order to effectively increase the copy number of the DNA sequence.

The "target sequence" is the sequence of bases in the target nucleic acid, and may refer to the sense and/or antisense strand of a double stranded target, and also encompasses, unless the context dictates otherwise, the same base sequence as reproduced or replicated in amplified copies, extension products or amplification products of the initial target nucleic acid.

The target sequence may be present in any kind of sample e.g. biological or environmental (water, air etc.). A biological sample may be, for example, a food sample or a clinical sample. Clinical samples may include the following: urine, saliva, blood, serum, plasma, mucus, sputum, lachrymal fluid or faeces.

The sample may or may not be subject to processing before being contacted with the primers. Such processing may include one or more of: filtration, concentration, partial-purification, sonication, lysis and the like. Such processes are well-known to those skilled in the art.

The method of the present invention involves the use of a nick site and means for creating a nick at the nick site. A "nick" is the cleavage of the phosphodiester backbone of just one strand of a fully, or at least partially, double stranded nucleic acid molecule. The nick site is the location in the molecule where a nick is made.

In preferred embodiments a "nicking recognition site" will be present at, within, or near to a nick site. ("Near to" in this context means that the nearest base of the nicking recognition site is within 10 bases of the nick site, preferably within 5 bases of the nick site).

The nicking recognition site may comprise at least one strand of the recognition site of a restriction endonuclease, and the nick site may comprise at least one strand of a nucleic acid base sequence which, when present as a double stranded molecule, is cut by a restriction endonuclease. Typically a restriction endonuclease will cut both strands of a double stranded nucleic acid molecule. In the present invention, a double stranded break can be avoided by the incorporation of one or more modified bases at or near to the nick site, which modified bases render a strand of nucleic acid not susceptible to cleavage by the restriction endonuclease. In this way a restriction endonuclease, which usually cuts both strands of a double stranded nucleic acid molecule, can be used to introduce a single stranded nick into a double stranded molecule. Modified bases and the like suitable for achieving this are well-known to those skilled in the art and include, for example, all alpha phosphate modified nucleoside triphosphates and alpha borano modified nucleoside triphosphates, specifically; 2'-deoxyadenosine 5'-O-(thiotriphosphate), 5-methyldeoxycytidine 5'-triphosphate, 2'-deoxyuridine 5'triphosphate, 7-deaza-2'deoxyguanosine 5'-triphosphate, 2'deoxyguanosine-5'-O-(1-boranotriphosphate) and others. Triphosphates including the modified base may be present within a reaction mixture used to perform the amplification process, so that modified bases are incorporated at relevant positions during subsequent rounds of amplification to prevent the formation of a site cleavable by the endonuclease.

In preferred embodiments however the nick is made at the nick site by means of a nicking enzyme. These are enzymes which, under normal circumstances, make only a single stranded break in a double stranded nucleic acid molecule. The nicking enzyme has a nicking recognition site and the nick site may be within the nicking recognition site or may be either 5' or 3' of the recognition site. Many nicking enzymes are known to those skilled in the art and are commercially available. A non-exhaustive list of examples of nicking enzymes includes: Nb.Bsml, Nb.Bts, Nt.Alwl, Nt.BbvC, Nt.BstNBI, and Nt.Bpu101. The latter enzyme is commercially available from ThermoFisher Scientific; the others are available from e.g. New England Biolabs.

In preferred embodiments, the nicking enzyme is introduced into the reaction mixture at the outset of the method (e.g. within one minute of contacting the sample with primers and DNA polymerase). However, in some instances it may be desirable to introduce the nicking enzyme into the reaction mixture after a longer delay (e.g. to allow the temperature to fall closer to the optimum temperature of the nicking enzyme).

The method of the invention involves the use of a DNA polymerase. Preferably the method of the invention comprises the use of at least one thermophilic DNA polymerase (i.e. having an optimum temperature in excess of 60° C.).

Preferably the DNA polymerase is a strand displacing polymerase. Preferably the DNA polymerase has no exonuclease activity. Preferably the DNA polymerase is a strand displacing polymerase with no exonuclease activity, and is also preferably thermophilic.

Examples of preferred DNA polymerases include Bst polymerase, VENT DNA polymerase, 9° N polymerase, MANTA™ 1.0 polymerase (Qiagen), BstX polymerase (Qiagen), and Bsm DNA polymerase, large fragment (ThermoFisher Scientific).

In some embodiments, the method of the invention may conveniently comprise a pre-amplification or enrichment step. This is a step in which the target sequence is contacted with forward and reverse primers and DNA polymerase, but no nicking enzyme. This typically lasts for about 2-5 minutes and produces an initial (linear) amplification of the target sequence of about 1,000 fold, which can be especially useful if the target sequence is present in the sample at low copy number.

In some embodiments, the pre-amplification or enrichment step is performed using a mesophilic DNA polymerase such as Exo-Minus Klenow DNA Polymerase or Exo-Minus psychrophile DNA polymerase from *Cenarchaeum symbiosum*, at a temperature below 50° C., and the mixture is subsequently heated above 50'C to denature or inactivate the thermolabile DNA polymerase, and then a thermophilic DNA polymerase is added for downstream amplification.

Typically, the method of the invention comprises a detection step, in which one or more of the direct or indirect products of the amplification process is detected and optionally quantified, this indicating the presence and/or amount of the target in the sample. There are a great many suitable detection and/or quantification techniques known, including: gel electrophoresis, mass spectrometry, lateral flow capture, incorporation of labelled nucleotides, intercalating dyes, molecular beacons and other probes, especially specifically hybridising oligonucleotides or other nucleic acid containing molecules.

The product or products which are detected in the detection step may be referred to herein as the "detection target". The 'target' in relation to the detection step, is not to necessarily the same as the 'target' in the amplification process and indeed the two molecules will usually be different to at least some extent, although they may have some sequence (typically 10-20 bases) in common, where the detection target comprises a nucleic acid molecule or oligonucleotide.

Nucleic acid detection methods may employ the use of dyes that allow for the specific detection of double-stranded DNA. Intercalating dyes that exhibit enhanced fluorescence upon binding to DNA or RNA are well known. Dyes may be, for example, DNA or RNA intercalating fluorophores and may include inter alia the following: acridine orange, ethidium bromide, Pico Green, propidium iodide, SYBR® I, SYBR® II, SYBR® Gold, TOTO-3 (a thiaxole orange dimer) OLI GREEN™ and YOYO™ (an oxazole yellow dimer).

Nucleic acid detection methods may also employ the use of labelled nucleotides incorporated directly into the detection target sequence or into probes containing sequences complementary or substantially complementary to the detection target of interest. Suitable labels may be radioactive and/or fluorescent and can be resolved in any of the manners conventional in the art. Labelled nucleotides, which can be detected but otherwise function as native nucleotides (e.g. are recognised by and may act as substrates for, natural enzymes), are to be distinguished from modified nucleotides, which do not function as native nucleotides.

The presence and/or amount of target nucleic acids and nucleic acid sequences may be detected and monitored using molecular beacons. Molecular beacons are hair-pin shaped oligonucleotides containing a fluorophore at one end and a quenching dye ("quencher") at the opposite end. The loop of the hair-pin contains a probe sequence that is complementary or substantially complementary to a detection target sequence and the stem is formed by the annealing of self-complementary or substantially self-complementary sequences located either side of the probe sequence. The hairpin comprises 5 to 10 base pairs.

The fluorophore and the quencher are bound at opposite ends of the beacon. Under conditions that prevent the molecular beacon from hybridizing to its target or when the molecular beacon is free in solution, the fluorophore and quencher are proximal to one another, preventing fluorescence. When the molecular beacon encounters a detection target molecule, hybridization occurs; the loop structure is converted to a stable, more rigid conformation causing separation of the fluorophore and quencher allowing fluorescence to occur (Tyagi et al. 1996, Nature Biotechnology 14: 303-308). Due to the specificity of the probe, the generation of fluorescence is substantially exclusively due to the presence of the intended amplified product/detection target.

Molecular beacons are highly specific and can distinguish nucleic acid sequences differing by a single base (e.g. single nucleotide polymorphisms). Molecular beacons can be synthesized with different coloured fluorophores and different detection target complementary sequences, enabling several different detection targets in the same reaction to be detected and/or quantified simultaneously, allowing "multiplexing" of a single PoC assay to detect a plurality of different pathogens or biochemical markers. For quantitative amplification processes, molecular beacons can specifically bind to the amplified detection target following amplification, and because non-hybridized molecular beacons do not fluoresce, it is not necessary to isolate probe-target hybrids to quantitatively determine the amount of amplified product. The resulting signal is proportional to the amount of the amplified product. This can be done in real time. As with other real time formats, the specific reaction conditions must be optimized for each primer/probe set to ensure accuracy and precision.

The production or presence of detection target nucleic acids and nucleic acid sequences may also be detected and monitored by fluorescence resonance energy transfer (FRET). FRET is an energy transfer mechanism between two fluorophores: a donor and an acceptor molecule. Briefly, a donor fluorophore molecule is excited at a specific excitation wavelength. The subsequent emission from the donor molecule as it returns to its ground state may transfer excitation energy to the acceptor molecule (through a long range dipole-dipole interaction). FRET is a useful tool to quantify molecular dynamics, for example, in DNA-DNA interactions as seen with molecular beacons. For monitoring the production of a specific product a probe can be labelled with a donor molecule on one end and an acceptor molecule on the other. Probe-detection target hybridization brings a change in the distance or orientation of the donor and acceptor and a change in the FRET properties is observed. (Joseph R. Lakowicz. "Principles of Fluorescent Spectroscopy", Plenum Publishing Corporation, $2^{nd}$ edition (Jul. 1, 1999)).

The production or presence of detection target nucleic acids may also be detected to and monitored by lateral flow devices. Lateral flow devices are well known. These devices generally include a solid phase fluid permeable flow path through which fluid flows by capillary force. Examples include, but are not limited to, dipstick assays and thin layer chromatographic plates with various appropriate coatings. Immobilized in or on the flow path are various binding reagents for the sample, binding partners or conjugates involving binding partners for the sample, and signal producing systems. Detection of analytes can be achieved in several different ways including: enzymatic detection, nanoparticle detection, colorimetric detection, and fluorescence detection. Enzymatic detection may involve enzyme-labelled probes that are hybridized to complementary or substantially complementary nucleic acid detection targets on the surface of the lateral flow device. The resulting complex can be treated with appropriate markers to develop a readable signal. Nanoparticle detection involves bead technology that may use colloidal gold, latex and paramagnetic nanoparticles. In one example, beads may be conjugated to an anti-biotin antibody. Target sequences may be directly biotinylated, or target sequences may be hybridized to a sequence specific biotinylated probes. Gold and latex give rise to colorimetric signals visible to the naked eye and paramagnetic particles give rise to a non-visual signal when excited in a magnetic field and can be interpreted by a specialized reader.

Fluorescence-based lateral flow detection methods are also known, for example, dual fluorescein and biotin-labelled oligo probe methods, or the use of quantum dots.

Nucleic acids can also be captured on lateral flow devices. Means of capture may include antibody dependent and antibody independent methods. Antibody-independent capture generally uses non-covalent interactions between two binding partners, for example, the high affinity and irreversible linkage between a biotinylated probe and a streptavidin capture molecule. Capture probes may be immobilized directly on lateral flow membranes.

The entire method of the invention, or at least the amplification process portion of the method, may be performed in a reaction vessel (such as a conventional laboratory plastics reagent tube e.g. from Eppendorf®) or may be performed in and/or on a solid support. The solid support may be porous or non-porous. In a particular embodiment the solid support may comprise a porous membrane material (such as nitrocellulose or the like). More especially the solid support may comprise or form part of a porous lateral flow assay device, as described above. Alternatively, the solid support may comprise or form part of a microfluidics-type assay, in which one or more solid narrow-bore capillary tubes are used to transport a liquid along an assay device.

In preferred embodiments, all or at least part of the method of the invention may be performed using a point-of-care (PoC) assay device. A PoC device typically has the following characteristics: it is cheap to manufacture, is disposed of after a single use, is generally self-contained not requiring any other apparatus or equipment to perform or interpret the assay and, desirably, requires no clinical knowledge or training to use.

Examples of primers suitable for use in the invention are disclosed herein. Other examples which may be suitable for use in the method of the invention are disclosed in, inter alia, US 2009/0017453 and EP 2,181,196, the content of both of which is incorporated herein by reference. The person skilled in the art will be readily able to design other primers suitable for the amplification of other target sequences without undue experimentation.

As explained elsewhere, primers of use in the invention will preferably comprise not only a target complementary portion, but also a nicking endonuclease binding site and nicking site, and a stabilizing portion. Preferred primers may contain self-complementary sequence which can form a stem-loop structure in the primer molecule.

Primers of use in the method of the invention may comprise modified nucleotides (i.e. nucleotides not found in naturally occurring nucleic acid molecules). Such modified nucleotides may conveniently be present in the target complementary portion of the primer, and/or elsewhere in the primer. Preferred examples of modified nucleotides are 2'-modified nucleotides, especially 2'O-methyl modified nucleotides, although many other modified nucleotides are known to those skilled in the art.

Temperature Profile

The method of the present invention, whilst not isothermal, does not require thermal cycling. As a result the method of the invention does not require the use of the relatively complex thermal cycling apparatus used in PCR, and accordingly lends itself more readily to application in a PoC context.

"Thermal Cycling" or temperature cycling means that, in particular, the temperature of a reaction mixture is held at a particular temperature (say ti) for a particular length of time (typically at least 30 seconds). The temperature is then adjusted (either up or down) before being returned to the previously maintained temperature.

Typically non-isothermal nucleic acid amplification reactions, such as PCR, require the performance of multiple thermal steps per cycle (i.e. at least two or more), and multiple thermal cycles per reaction.

The temperature reduction in the method of the present invention is deliberate, and controlled, in the sense that the magnitude of the temperature reduction is above a predetermined minimum level and below a predetermined maximum level. In addition, the rate of temperature decrease is preferably within a predetermined range.

The initial step (a) in the method of the invention involves contacting a target sequence with a primer having at least a portion which is complementary to the target sequence, in conditions which permit the primer to hybridise to the target, at least temporarily. This may be described as the "initiation" phase.

This step is typically accomplished at a temperature in the range 50-65° C., preferably in the range 52-62° C., more preferably in the range 54-62° C., most preferably in the range 58-62° C. The reaction mixture comprising the target and the primer may be held at this temperature for a suitable period of time. The optimum temperature, and the optimum period of time for which the reaction mixture is held at this temperature, may be determined by the person skilled in the art given the benefit of the present disclosure, and these may be affected by parameters such as the length of the target sequence, the length of the primers—and especially the length of the portion of the primer which is complementary to the target, the G:C content of the target: primer hybrid, the pH and salt concentration of the reaction mixture. A typical initial temperature holding time might be in the range 5 seconds to 5 minutes, preferably 10 seconds to 3 minutes. Typical conditions to permit the initial hybridisation event in step (a) will be known to those skilled in the art and are described in the accompanying examples.

The temperature range of 58–62° C. is preferred for the initiation phase. This is thought to be sufficiently high to minimise the formation of primer dimers (and hence to reduce the amount of non-specific amplification), and increase the probability of creating potential "initiation sites" in the target duplex, whilst being low enough to allow at least some of the primer molecules to hybridise to the target.

The subsequent reduction in temperature helps stabilise the hybridisation of the relatively short primers and the extension products, rather than hybridisation of the primers to the original target molecule. It is further hypothesized that additional cooling of the reaction mixture facilitates hybridisation of the detection probe to the detection target.

During the amplification process set out in steps (b)-(d) of the method, the temperature of the reaction mixture is reduced. This may be done in a regulated manner, for example, using a temperature regulation means to reduce the temperature of the reaction mix according to a predetermined temperature profile. The temperature reduction may commence immediately after the initiation phase (step a). Advantageously the volume of the reaction mix is small, so that the thermal capacity of the reaction mix (and the reaction vessel or substrate in or on which the reaction is performed) is reduced.

Conveniently the reaction mix has a volume of less than 100μl, preferably less than 50 μl, more preferably less than 25μl and most preferably less than 20μl. In this way, the temperature of the reaction mix can be more accurately and more swiftly regulated by the temperature regulation means. In suitable embodiments the temperature regulation means may be very simple (e.g. a fan) or may be dispensed with entirely, with sufficient cooling being largely or wholly achieved by passive means (e.g. by thermal radiation from the reaction mixture). Typically the reaction mix volume may be in the range 1-50 μl, preferably 1-20 μl and more preferably 1-10 μl.

The reaction mix volume may be less than 10 μl. In particular, the method of the invention may employ a "digital PCR"-type approach (see review by Morley 2014

Biomolecular Detection and Quantification 1, 1-2) in which the sample is diluted and split into many (usually several hundred, a few thousand, or even million) aliquots which are processed in parallel: some of the aliquots will contain a target sequence and some will not: if no target sequence is present no signal is generated. The proportion of negative aliquots can be used to deduce the number and/or concentration of the target sequence in the original sample. In such embodiments, the reaction mix volume in each aliquot may be very small, typically however the minimum volume would be 2500 nl, preferably at least 50 µl.

The temperature may be reduced in any desired profile. For instance, the temperature may be reduced according to a substantially linear profile (i.e. with an essentially constant rate of temperature reduction), or may be reduced in any non-linear manner, including a curve or a step-wise fashion, or any combination of linear and non-linear profiles (e.g. one or more periods of constant rate temperature reduction, which rate may be zero or relatively low, alternating with periods of relatively high rates of temperature reduction).

The temperature profile of the reaction in accordance with the invention is such that the temperature of the reaction is not allowed to return to the temperature at which the "initiation" phase is performed. Thus in the method of the present invention there is no oscillation about a predetermined temperature and no "return" to a predetermined temperature contrary to, for example, the disclosure of WO 2011/030145.

The temperature of the reaction mix at the start of the amplification process will typically be the same as that in step (a) e.g. preferably in the range 54-62° C. and most preferably 58-62° C. During the amplification process, the temperature falls by at least 2° C., preferably by at least 3, 4 or 5° C., more preferably by at least 8, 9 or 10° C., and most preferably by at least 13, 14 or 15° C., although it will be appreciated that the preferred magnitude of the temperature drop, in absolute terms, may be at least partially dependent on the selected initial temperature at the start of the amplification process, wherein a lower initial temperature (e.g. in the range 45-55° C.) might predicate a lower temperature drop and/or a lower rate of temperature reduction. Typically the maximum magnitude of the temperature decrease during the amplification process is about 20° C., although it will be appreciated that the maximum temperature decrease might be less than this (e.g. 16, 17, 18 or 19° C.) or more (e.g. 25 or 30° C.).

In preferred embodiments the magnitude of the temperature reduction of the reaction mix during the amplification process may be in the range 5-40° C., preferably in the range 8-35° C., more preferably in the range 8-30° C. or even 8-25° C., and most preferably in the range 8-20° C. The typical initial temperature of the reaction mixture at the start of the amplification process is in the range 50-62° C., preferably 54-62° C., more preferably in the range 56-60° C., and most preferably in the range 58-60° C.

In preferred embodiments, the temperature reduction during the amplification process (steps (b)-(d) of the method of the invention) includes a reduction encompassing the range 54 to 50° C., 56 to 50 or 58 to 50, more preferably 58 to 45, 58 to 40 or even 60 to 40° C. It will be understood that the temperature reduction during the amplification process may be greater than the stated ranges defined above. That is, the maximum temperature may exceed the upper temperature of the stated range and/or the minimum temperature may be beneath the lower temperature of the stated range.

The end temperature of the amplification reaction is preferably selected for compatibility with the chosen detection method. For example, if the detection method involves the use of an enzyme label, it may be desirable to arrange the end temperature of the amplification reaction to be compatible with the enzyme and, for example, within ±5° C. of the optimum temperature of the enzyme. Alternatively, where the detection method involves the use of a hybridising detection probe, such as a molecular beacon or the like, it will be advantageous to arrange the end temperature of the amplification reaction to be selected so as to be compatible with the Tm of the detection probe/detection target duplex.

For example, the end temperature may conveniently be below the Tm of the detection probe/detection target duplex, preferably at least 2° C. below, so as to facilitate the hybridisation of the probe to the detection target.

The typical average rate of temperature reduction during the amplification process is in the range $-0.10$ to $-6.0°$ C. $\text{min}^{-1}$, preferably in the range $-0.20$ to $-3.5°$ C. $\text{min}^{-1}$, more preferably in the range $-0.30$ to $-3.5°$ C. $\text{min}^{-1}$, and most preferably in the range $-0.40$ to $-3.5°$ C. $\text{min}^{-1}$. As will be apparent from the foregoing, the actual rate of temperature reduction at any one instant during the amplification process might deviate from the preferred average rate, depending on the nature of the temperature reduction gradient.

In some embodiments the temperature reduction gradient is substantially linear for at to least 3 minutes, more preferably at least 4 minutes and most preferably over most of the duration of the amplification process. Typically the temperature reduction gradient is substantially linear over a period in the range 3-12 minutes, preferably in the range 4-10 minutes, more preferably in the range 4-8 minutes. For present purposes "substantially linear" means that, for any second order polynomial describing the temperature gradient, the magnitude of the coefficient of X is less than 5% of the value of the coefficient of Y.

A large number of different techniques can be envisaged for achieving the desired temperature reduction during the amplification process. These may include one or both of the following: (a) ceasing to apply heat to the reaction mix and/or removing the reaction mix from a heated and/or insulated environment and allowing the reaction mix to cool essentially by passive heat-loss to the ambient environment; (b) application of active cooling to the reaction mix. Active cooling may involve exposing the reaction mix to a cooled environment e.g. placing the reaction mix in thermally communicating (conducting, radiating or convection) contact with a cooled medium, especially a fluid. This could comprise, for example, contacting the reaction mix with a chilled water bath, using a fan to blow cold air or other gas over or through the reaction mix, contacting the reaction mix with a reaction mix-compatible coolant, which may be a gas, liquid or solid, or the use of a Peltier-type cooling device. For example, the reaction mix-compatible coolant may be a reaction mix compatible buffer in frozen or chilled liquid form. The addition of a cold buffer would tend to dilute the reaction mix, so if this approach is adopted it may be preferred to use small volumes (e.g. less than 1-2µl) of coolant at a temperature well below (i.e. more than 20° C. cooler than) the temperature of the reaction mix.

Any active cooling steps may be applied discontinuously during the amplification process so as to achieve a desired temperature reduction level and/or a desired temperature reduction profile. In particular, active cooling may be performed at two or more interspersed intervals during the amplification process, and may optionally be combined with passive cooling, simultaneously or alternating.

In general, it is preferred to achieve the desired amount and rate of temperature reduction substantially by purely passive means, since this simplifies the method and any apparatus or kit required for performing the method. In order to achieve the desired amount and rate of cooling by substantially purely passive means, it is desirable that the volume of the reaction mix is small, so as to reduce its thermal capacity, as noted previously.

It is a preferred feature of the method of the invention that the amplification process may utilise a first polymerase having an optimum temperature, and a second polymerase having an optimum temperature, wherein the optimum temperature of the second polymerase is lower than the optimum temperature of the first polymerase. Accordingly, the first polymerase may be especially active near the start of the amplification process, since the temperature of the reaction mix may be at or close to the optimum temperature of the first polymerase.

Thus, for example, the first polymerase may advantageously be a "thermophilic" enzyme (i.e. having an optimum temperature in excess of 60° C.).

Conversely, the second polymerase has a lower optimum temperature than the first polymerase. As the amplification process continues, the temperature of the reaction mix falls and approaches closer to the optimum temperature of the second polymerase. Thus the second polymerase becomes increasingly active, which at least partially compensates for a declining rate of reaction, which decline is due to (i) a general thermodynamic slowing of the reaction due to the lower temperature and (ii) the temperature of the reaction mix possibly falling below the optimum temperature of the first polymerase, resulting in reduced catalysis.

Advantageously the optimum temperature of the second polymerase is in the range 30-55° C., more preferably in the range 30-45° C.

In a particular embodiment the second polymerase may be Klenow fragment of DNA polymerase I or Bsu polymerase.

It is conceivable that even a third or further polymerase, preferably with a yet lower, third optimum temperature, may be used.

The second polymerase is preferably in the reaction mix from the outset of the amplification process but, if desired, the second polymerase could be added after a delay, allowing the temperature of the reaction mix to be reduced from a high initial temperature. This may be advantageous if, for example, the second polymerase is especially thermolabile and likely to be substantially denatured if present at the relatively high temperatures normally employed at the start of the amplification process.

In a manner exactly analogous to the foregoing, the amplification process may utilise first and second nicking enzymes with, respectively, higher and lower optimum temperatures. The first and second nicking enzymes may be used in conjunction with a single polymerase or multiple polymerases as the case may be.

As above, the use of a second nicking enzyme with a lower optimum temperature may at least partially offset the reduced rates of reaction expected as the temperature falls during the amplification process.

Thus, in some embodiments, the temperature of the reaction mix may start at, or may be reduced during the course of the amplification process to, a temperature below the optimum temperature of the first polymerase and/or the first nicking enzyme and will tend to approach, and may even reach, the optimum temperature of the second polymerase and/or second nicking enzyme.

Conveniently, in some embodiments, the method of the invention may comprise the step of contacting the reaction mixture with a degradative enzyme which degrades nucleic acid. Desirably this step is not effected until a user has obtained the desired outcome of the amplification reaction (e.g. detection of a pathogen). Typically therefore the degradative enzyme is added to the reaction mixture after the amplification process has reached a desired end-point. Preferably the degradative enzyme is thermolabile so that, in the event that it is inadvertently introduced into or contacted with reaction mix before the amplification process has attained the desired end-point, the temperature is sufficient to substantially denature or otherwise inactivate the enzyme. Suitable examples include cod uracil-DNA glycosylase ("UDG") available from ArcticZymes® and Antarctic thermolabile UDG (available from New England BioLabs). These enzymes are rapidly and irreversibly inactivated upon exposure to a temperature of 55° C. or 50° C. respectively, and the term "thermolabile" in relation to the degradative enzyme, should be construed accordingly. Alternatively, a thermally-sensitive degradative enzyme could be used (i.e. one which is at least partially active below 50° C. but, reversibly, substantially inactive above 55° C.).

BRIEF DESCRIPTION OF THE DRAWINGS

The invention will now be further described by way of illustrative example and with reference to the accompanying drawings, in which.

EXAMPLES

Example 1: Protocols for Testing Temperature Decreases

The effect of temperature decrease on an amplification reaction was tested by comparing amplifications using temperature decreases over time vs standard isothermal conditions. The decreasing temperature amplification is referred to herein as "STAR" (Selective Temperature Amplification Reaction). These comparisons were carried out using a protocol as described below unless noted.

Enzymes, Oligonucleotides, and Target

*Chlamydia trachomatis* (Ct) was used as the initial target for the development of the STAR mechanism. *Chlamydia trachomatis* Serovar J (ATCC VR-886) genomic DNA was acquired from American Type Culture Collection (Manassas, Va.). The open reading frame 6 region of the cryptic plasmid was amplified with primers STARctF61a (SEQ ID NO: 1, 5'-CGACTCCATATGGAGTCGAT-TTCCCCGAATTA-3') and STARctR61c (SEQ ID NO: 2, 5'-GGACTCCACACGGAGTCTTTTTCCTTGTTTAC-3'). The resulting DNA template was detected using a molecular beacon STARctMB1 (SEQ ID NO: 3, 5'-FAM/ccat-tCCTTGTTTACTCGTATTTTTAGGaatgg/BHQ1-3') as described in EP No. 0728218. MANTA™ 1.0 DNA polymerase was purchased from Enzymatics (Beverly, Mass.). Nt.BstNBI nicking endonuclease was purchased from New England BioLabs (Ipswich, Mass.) described in U.S. Pat. No. 6,191,267.

Figure 1A:
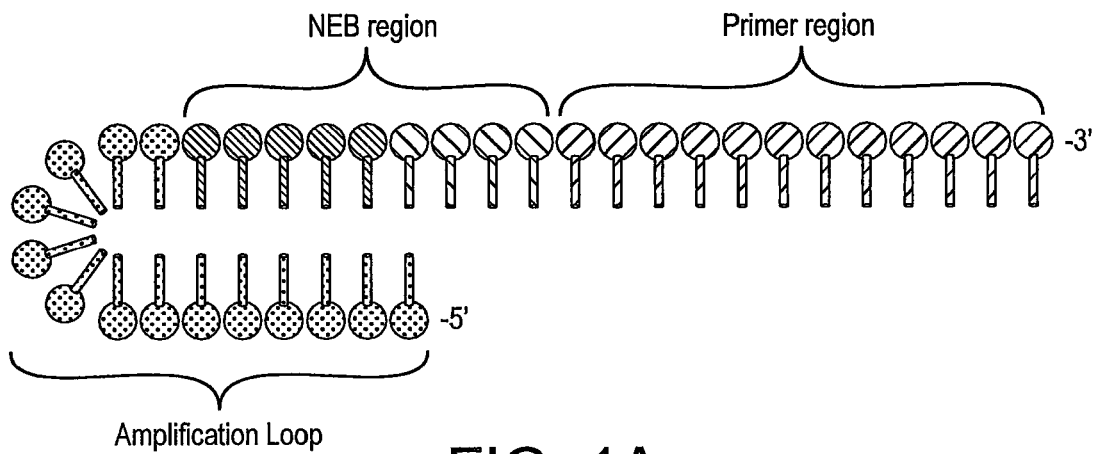
FIGS. 1A-1C are schematic representations of a typical embodiment of a primer useful in performing the method of the invention.

Oligonucleotides and molecular beacons were synthesized by Integrated DNA Technologies (Coralville, Iowa) and Bio-Synthesis (Lewisville, Tex.). The general features of the primers used in the STAR reactions were as follows:

Primer sets were constructed with a stabilizing region 5' of the nick site and a target specific binding region 3' of the nick site (FIG. 1A). Primers were constructed in such a way that a stem and loop structure can form at the 5' end of the oligonucleotide by creating a self-complementary structure that forms at least part of the stem. The $T_m$ of this structure was chosen to direct either linear or exponential amplification dependent upon the temperature of the reaction at a given time. The stem further encompassed at least a portion of the nicking enzyme recognition sequence. The nicking enzyme recognition sequence in the primers is part of the double stranded stem structure, but at least one nucleotide is single stranded to prevent nicking. If desired, the sequence that is complementary to the target sequence may comprise a secondary structure or may be free of secondary structure. Further, this sequence may contain modified nucleotides such as 2' modifications or phosphorothioate bonds.

Figure 1B:
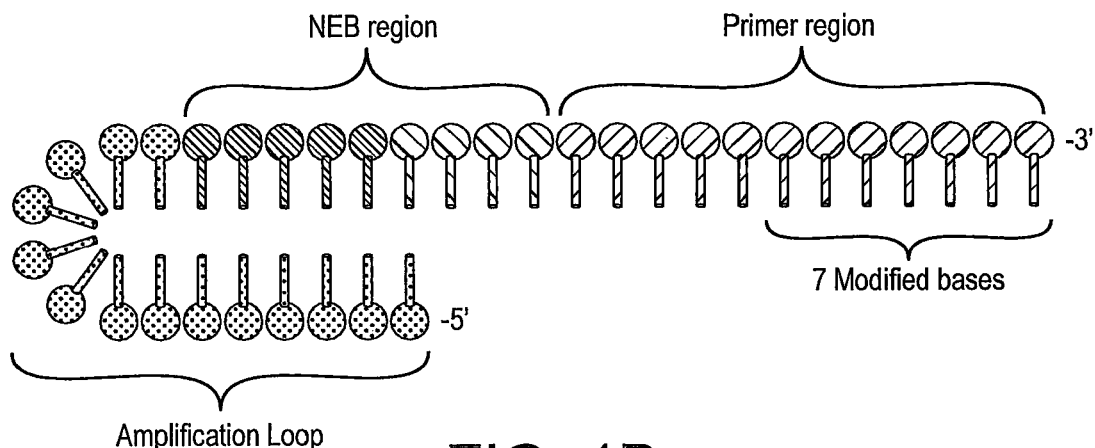
Figure 1C:
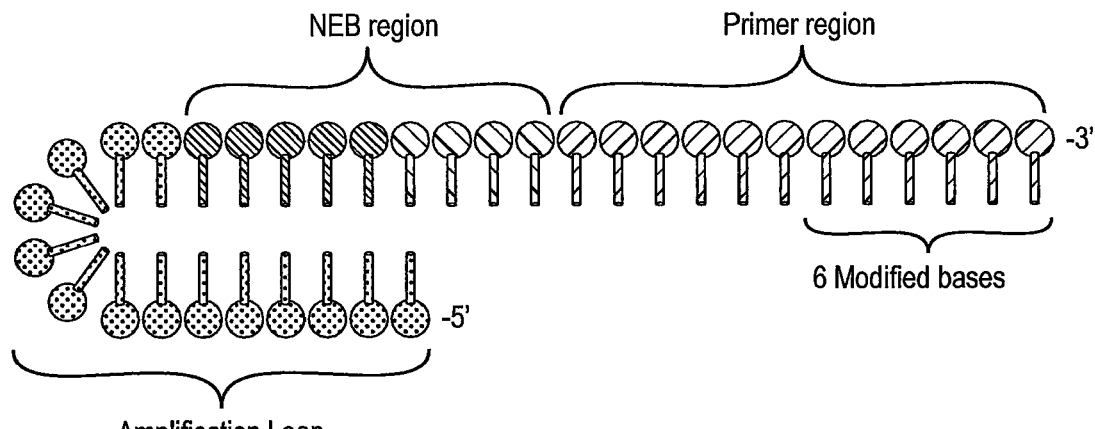

Referring to FIG. 1A, the "primer region" is the sequence that is complementary to, and anneals to, the target sequence. The "NEB region" is the nicking endonuclease binding region i.e. the recognition region of the nicking enzyme which, in this instance, nicks the primer at a site four nucleotides downstream of the end of the NEB region. The "Amplification loop" provides primer stabilization and hybridization for the amplification process and is looped on itself via self-complementarity during the initiation phase to reduce background non-specific amplification. FIGS. 1B and 1C show slightly different embodiments of primers useful in the method of the invention. The primer structure is essentially identical to the embodiment shown in FIG. 1A, but the altered primers include modified bases in the "primer region". Specifically at the 3' end of the primer region there is a string of consecutive 2'O-methylated bases. In FIG. 1B this string is 7 bases long and in FIG. 1C the string is 6 bases long. Primers of the sort shown in FIGS. 1B and 1C were used in Example 8 below.

Figure 2A:
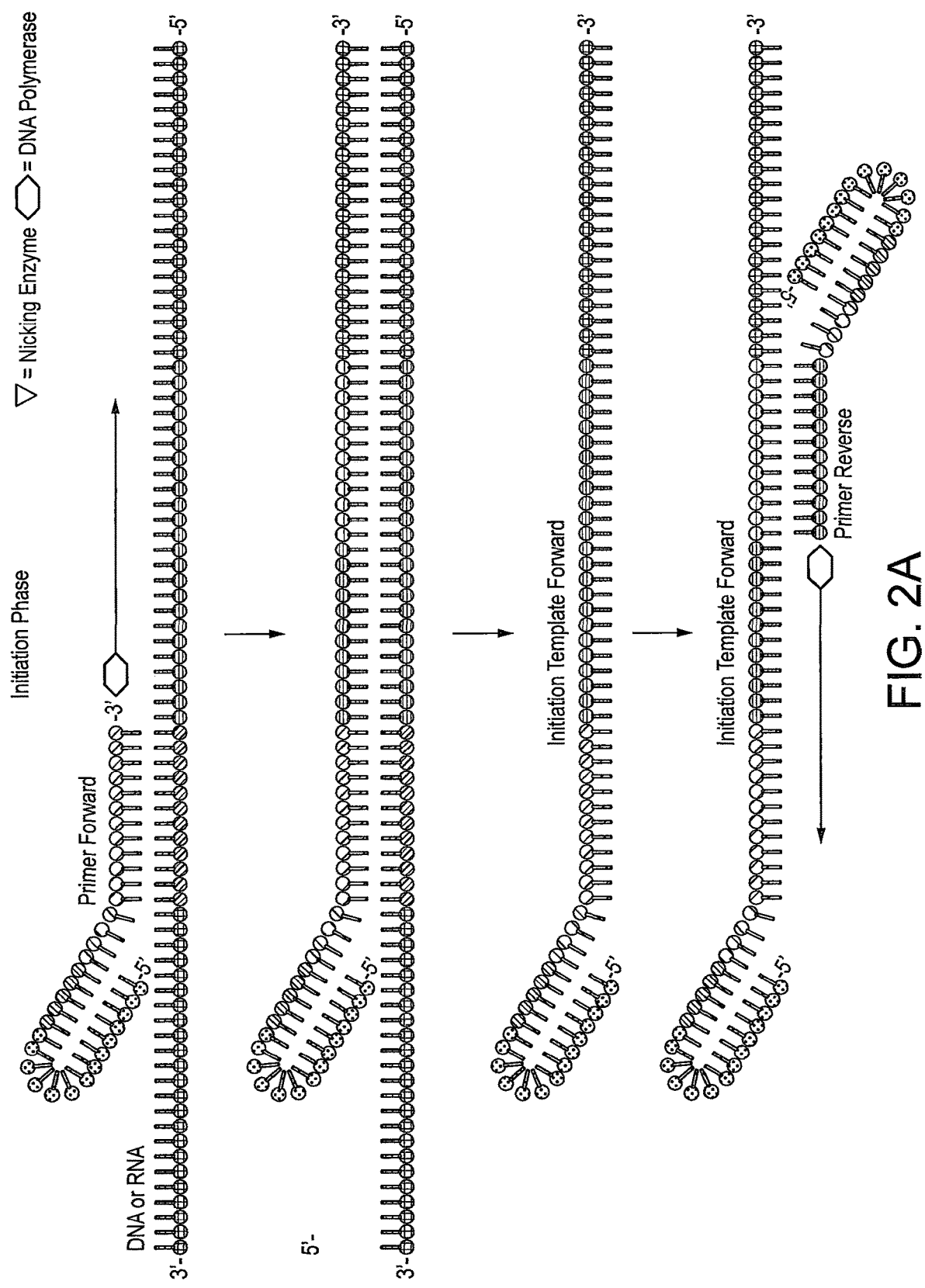
FIGS. 2A and 2B are schematic representations of the initiation phase and exponential amplification phase respectively of a nucleic acid amplification reaction suitable for performing the method of the invention.
Figure 2A:
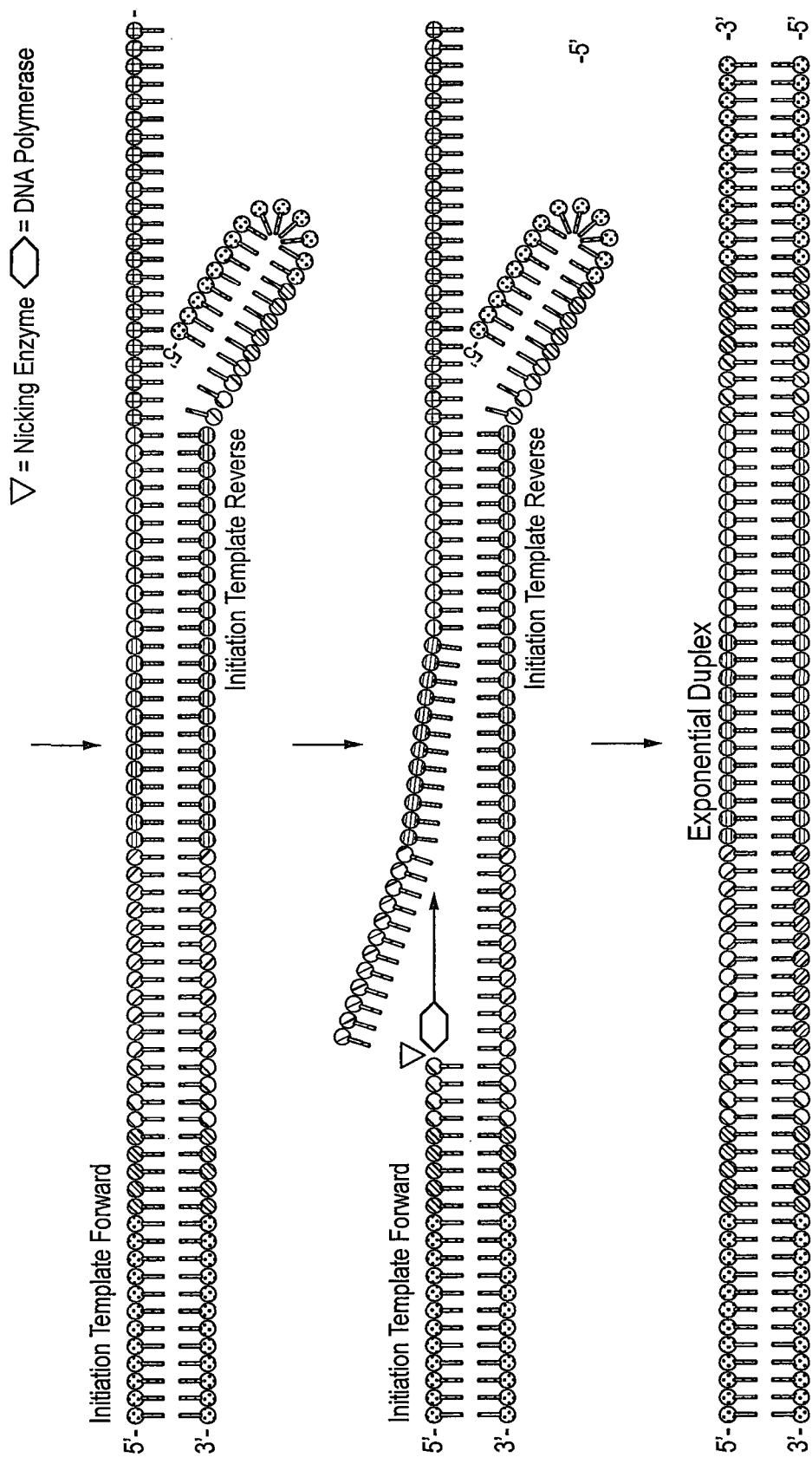
Figure 2B:
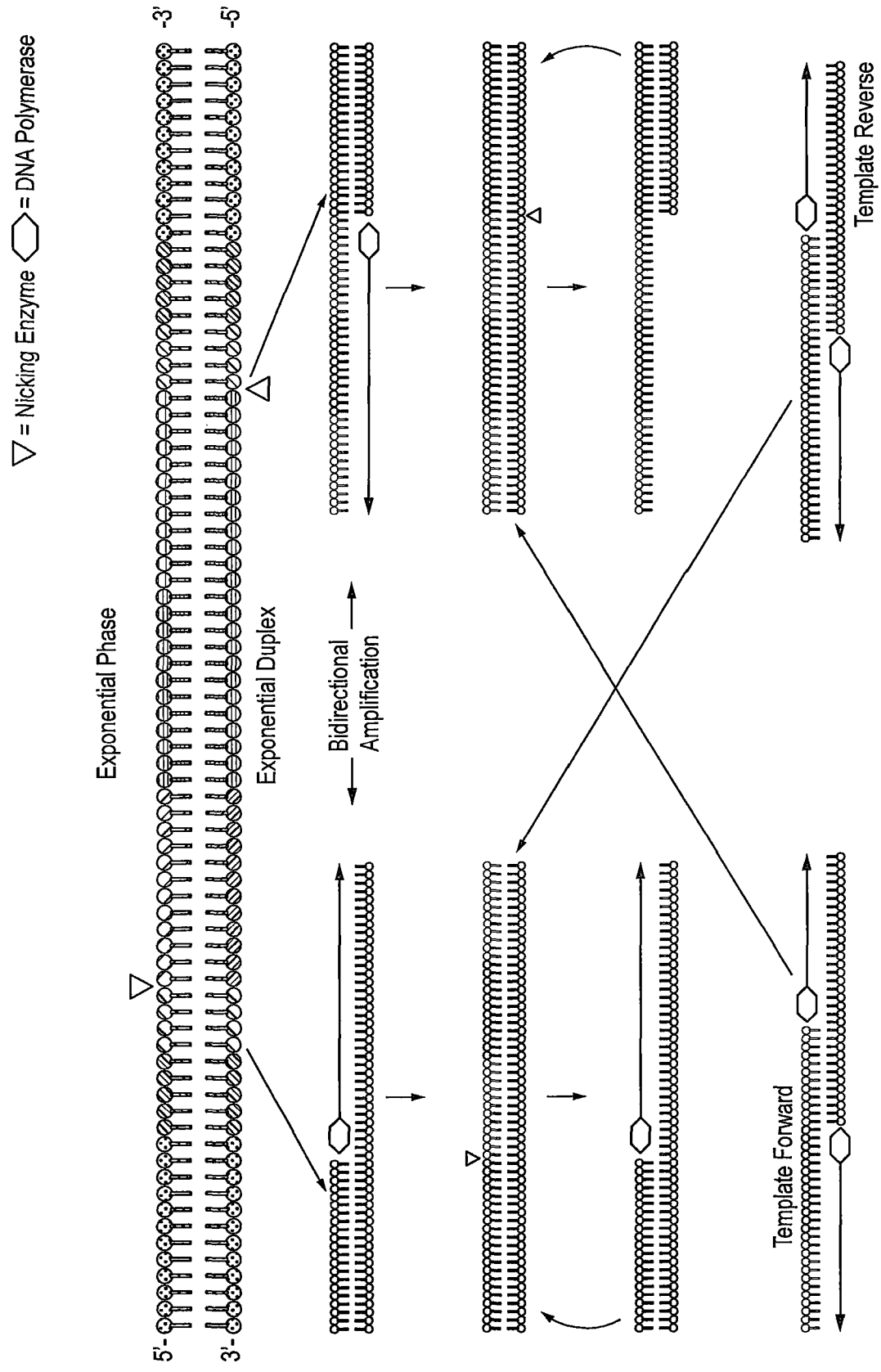

The summary of the oligonucleotides and amplification mechanism found in a reaction comprises (1) a target nucleic acid molecule; (2) two or more primer oligonucleotide molecules comprising some number of oligonucleotides that are complementary to the target nucleic acid molecule and (3) a site within the primer that can be nicked by a nicking enzyme. The method involves contacting a target nucleic acid molecule with a polymerase, two or more primer oligonucleotides, each of which specifically binds to a complementary sequence on the target nucleotide molecule, and a nicking enzyme; and, under non-isothermal conditions, generating a detectable amplicon that comprises at least a portion of a primer oligonucleotide that binds a target sequence. The overall STAR reaction can be understood to undergo two distinct phases; initiation and exponential amplification. The initiation phase is the initial formation of an exponential—template duplex from which exponential amplification can occur. These two phases are illustrated schematically in FIGS. 2A and 2B. In those figures, the triangle symbol represents the nicking enzyme and the hexagon symbol represents the DNA polymerase. Initial contact of the primer to a target nucleic acid occurs followed by extension and generation of a forward initiation template. Then the opposite strand primer binds to the newly generated forward initiation template, extending in the direction toward, and through, the initiation template's nick site. This initial process can be understood to involve the polymerase for extension and is highly prone to primer dimer-formation and false amplification of truncated or background products. Once nicking begins on either strand the polymerase will infiltrate the nick site and extend toward the opposite primer and through the nick site.

Once this cycle of nicking followed by polymerase extension has occurred on both the forward initiation strand and reverse initiation strand, a duplex is formed known as an exponential duplex. The second phase of the reaction begins; this exponential process of amplification feeds into itself as each new template generated from a nick and extension is now a target for another primer.

It is now understood that the second phase requires an active nicking endonuclease for fast template generation. It was previously known that this nick strand displacement replication occluded the need for temperature cycling thus the reaction could, and has always been, performed at constant temperature. The present novel discovery allows for unique and distinct amplification methods with significantly greater performance than existing methods, including high yield of product with great specificity in a short time period.

Amplification Conditions

The basic Selective Temperature Amplification Reaction (STAR) mixture contains two primers, polymerase and nicking enzyme (referenced above). The reactions were performed in a final volume of 20 µl, including 0.41 µM of the forward primer, 0.2 µM of the reverse primer, 0.18 µM molecular beacon, 10µl STAR Master Mix and 5 µl DNA sample. STAR master mix contains the following reagents; 15 mM MgSO$_4$, 90 mM Tris-HCl (pH 8.5), 300 µM each dNTPs, 15 mM (NH$_4$)$_2$SO$_4$, 15 mM Na$_e$ SO$_4$, 1 mM DTT, 0.01% TRITON X-100, 7 U nicking endonuclease, 48 U polymerase. The temperature of the reactions was isothermal or varied based upon the amount of temperature reduction. If the temperature during amplification in each reaction starts at 60° C. and decreases a specified amount every 15 seconds or 1 minute, then for example a negative 0.5° C. rate (i.e. a 0.5° C. decrease in temperature every 15 seconds) for 10 minutes would result in a temperature reduction from 60° C. to 40° C. over the course of the reaction. Amplification and STAR product detection were performed with the Agilent Mx3005P QPCR apparatus (Agilent). The following table lists the temperature profiles tested, except where noted:

TABLE 1

| Isothermal Conditions | | | |
|---|---|---|---|
| pre-reaction | Start | Temperature | Finish |
| 60° C. | 60° C. | none | 60° C. |
| 56° C. | 56° C. | none | 56° C. |
| 50° C. | 50° C. | none | 50° C. |

| STAR Conditions | | | |
|---|---|---|---|
| pre-reaction incubation | Start | Temperature Decrease | Finish |
| 60° C. | 60° C. | −0.1° C. per 15 seconds | 56° C. |
| 60° C. | 60° C. | 0.2° C. per 15 seconds | 52° C. |
| 60° C. | 60° C. | −0.5° C. per 15 seconds | 40° C. |
| 60° C. | 60° C. | −0.8° C. per 15 seconds | 32° C. |
| 60° C. | 60° C. | −1.0° C. per 15 seconds | 20° C. |
| 60° C. | 60° C. | −1.0° C. per minute | 51° C. |

The pre-reaction incubation is to allow the reagents to come to temperature to test the effect of decreasing temperatures on amplification kinetics, enzyme performance, and signal fluorescence. Running reactions in this manner removes increasing temperature variables and allows for a direct comparison between existing isothermal amplification techniques and the novel STAR method.

Amplification Procedure

The exact steps under which an amplification reaction was performed are as follows: 1) prepare master mix; 2) prepare primers with target or no target; 3) add primer mixes to row A-G of a 96 well plate dependent on number of reactions to be done per plate; 4) add master mix to row H of the same 96 well plate; 5) seal plate and do a pre-reaction incubation for 2 minutes; 6) transfer master mix from row H to each primer mix row, waiting 15 seconds between transfers; 7) seal and initiate preselected temperature profile and data collection.

During the course of a reaction amplified product was measured every 15 seconds by using the molecular beacon as described above. The fluorescence of the molecular beacon in the reaction mixture was monitored to measure the amount of specific product being generated during a reaction. Specific product generated during a reaction binds to the molecular beacon separating the fluorophore from the quencher, generating fluorescence. Fluorescence measurements were background subtracted based upon the average of the first 3 readings of each reaction well, before amplification begins. Further characterization was done based upon a rise from baseline threshold level (TL). The TL was chosen close to the baseline of the background subtracted fluorescence but above the range of random fluctuations. The decrease in temperature causes molecular beacon baseline fluorescence to decrease due to increased stem strength, causing a constant linear baseline decrease as the quencher and fluorophore have greater interaction. The TL of 2000 was chosen for all reactions. For comparison an exact number was determined based on time to amplification to reach the TL, referred to as the $A_T$ value. Using the $A_T$ value allows for comparisons from one plate to another.

Example 2: Results Using Unmodified Primers

To demonstrate the improvement that STAR provides over current isothermal technologies, amplifications were carried out using 18 replicates for target and 6 replicates for no target. The STAR reactions show a dramatic improvement in speed, sensitivity, and total fluorescence in comparison to isothermal conditions. In particular, the range of −0.8° C. minute to −3.2° C. minute was markedly better than all isothermal conditions (FIGS. 3 to 11). It is surprising and unexpected that such a significant drop in temperature still generates excellent results. Without limiting the Applicant to any particular theory, it is believed that the amplification improvements can be attributed to at least three characteristics, discussed further below.

The results of experiments using unmodified primers are shown in FIGS. 3-11. In those figures, the temperature profile is indicated by the background shading. The amount of signal (fluorescence) for the "non-target" negative controls is indicated by the dark plot. The amount of signal generated in the presence of 10 or 100 copies of target (genomic DNA of *C. trachomatis*) is indicated by the lighter plots.

Figure 3:
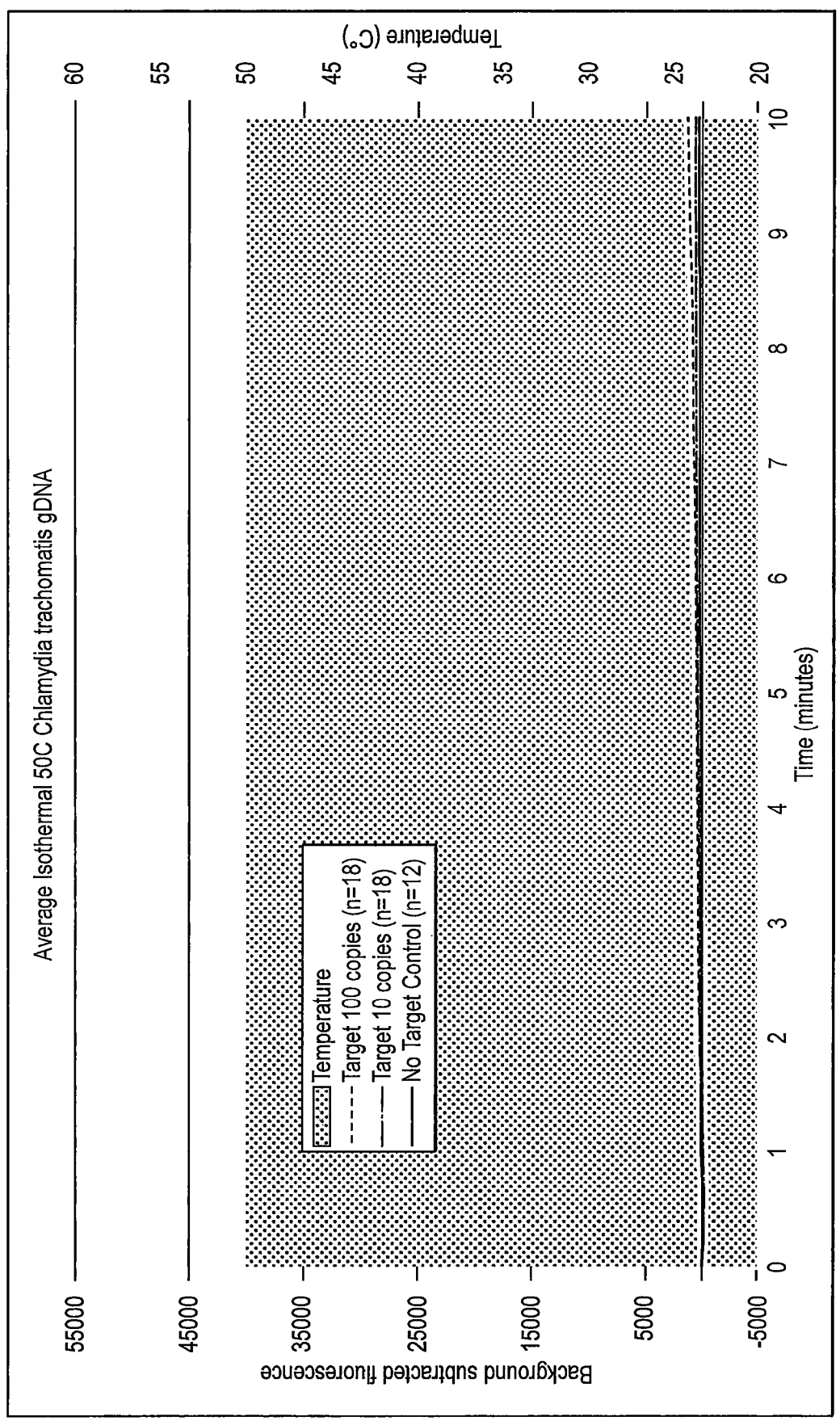
FIGS. 3 to 11 are graphs of (background substracted) fluorescence (arbitrary units) and temperature (° C.) against time (minutes)
Figure 4:
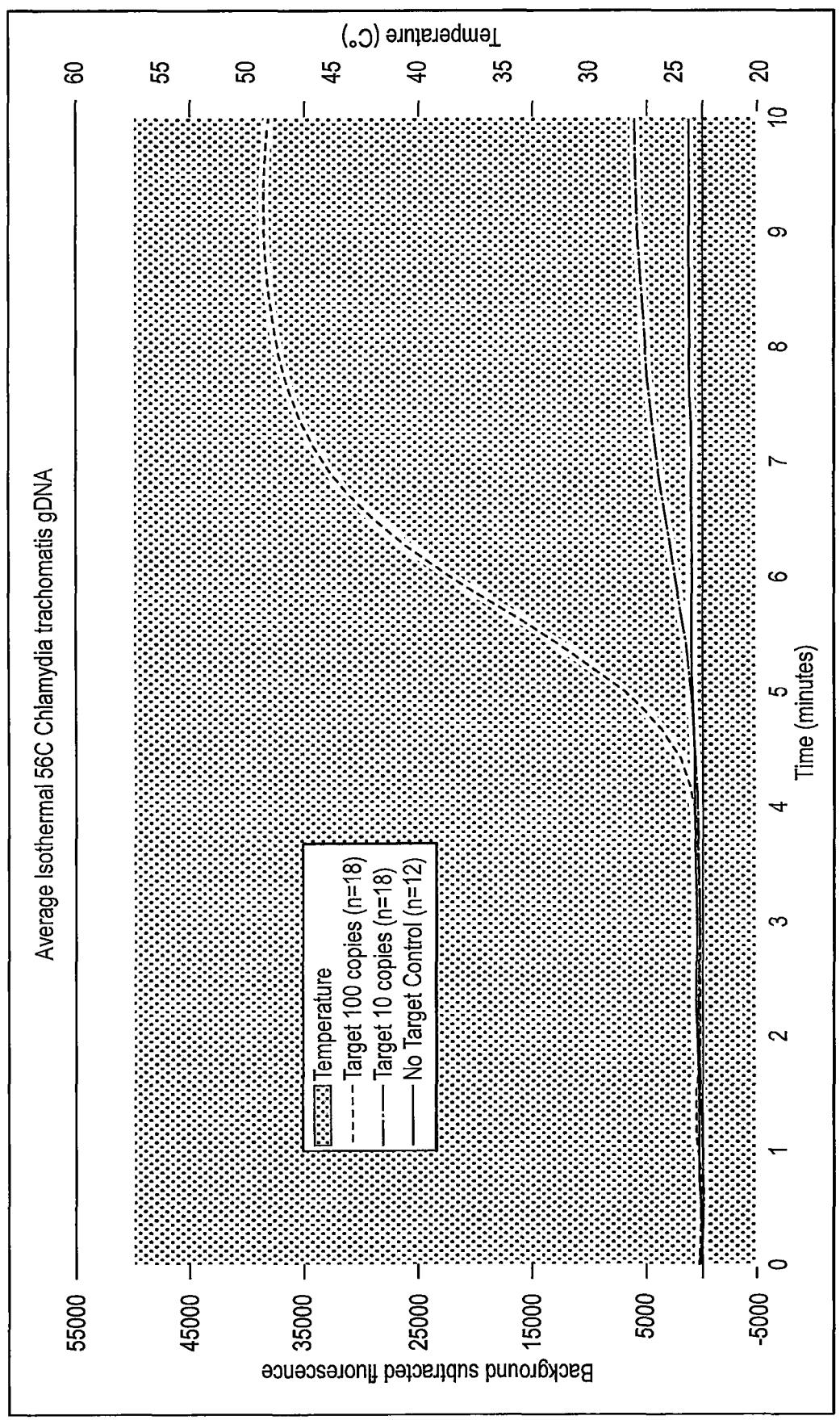
Figure 5:
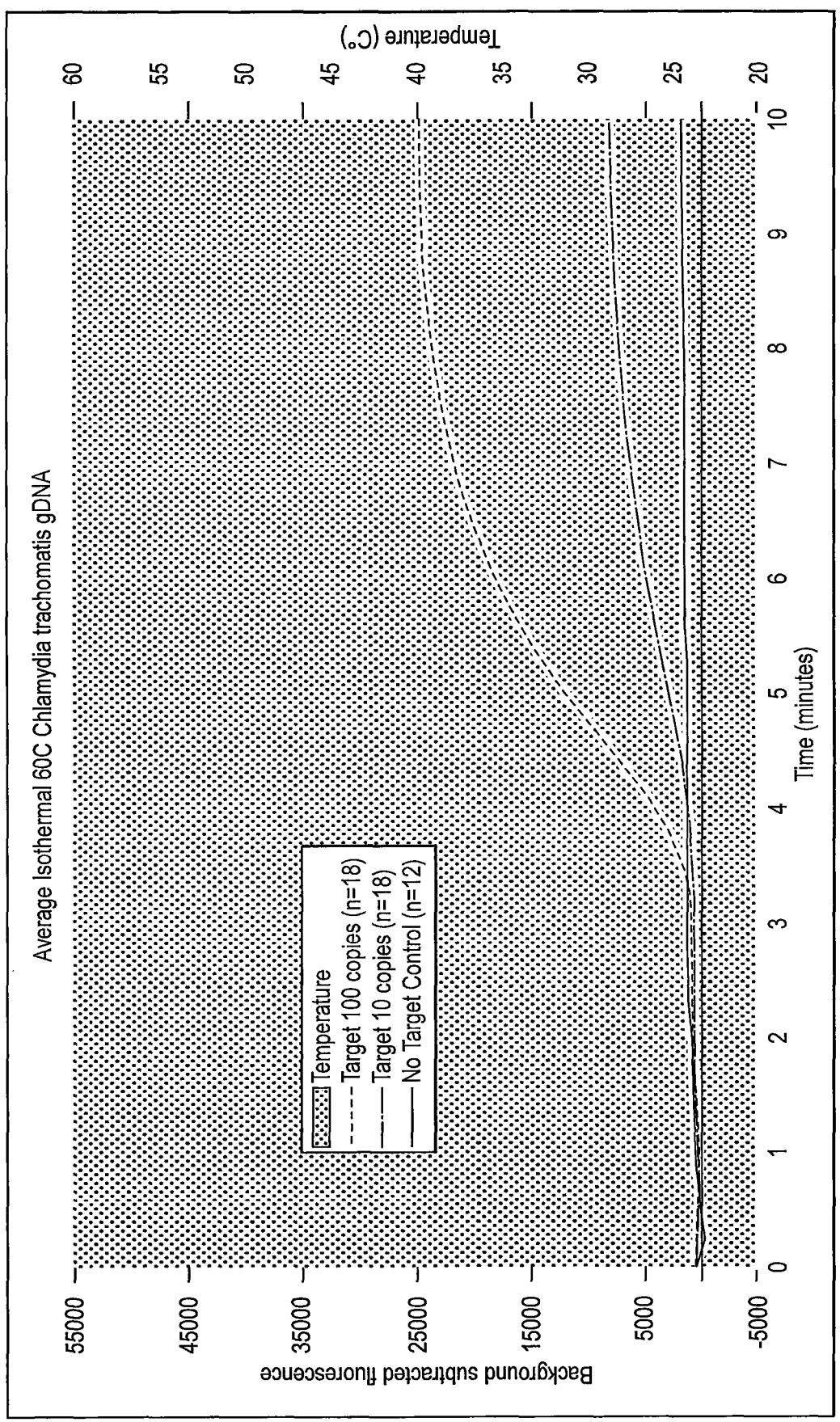
Figure 6:
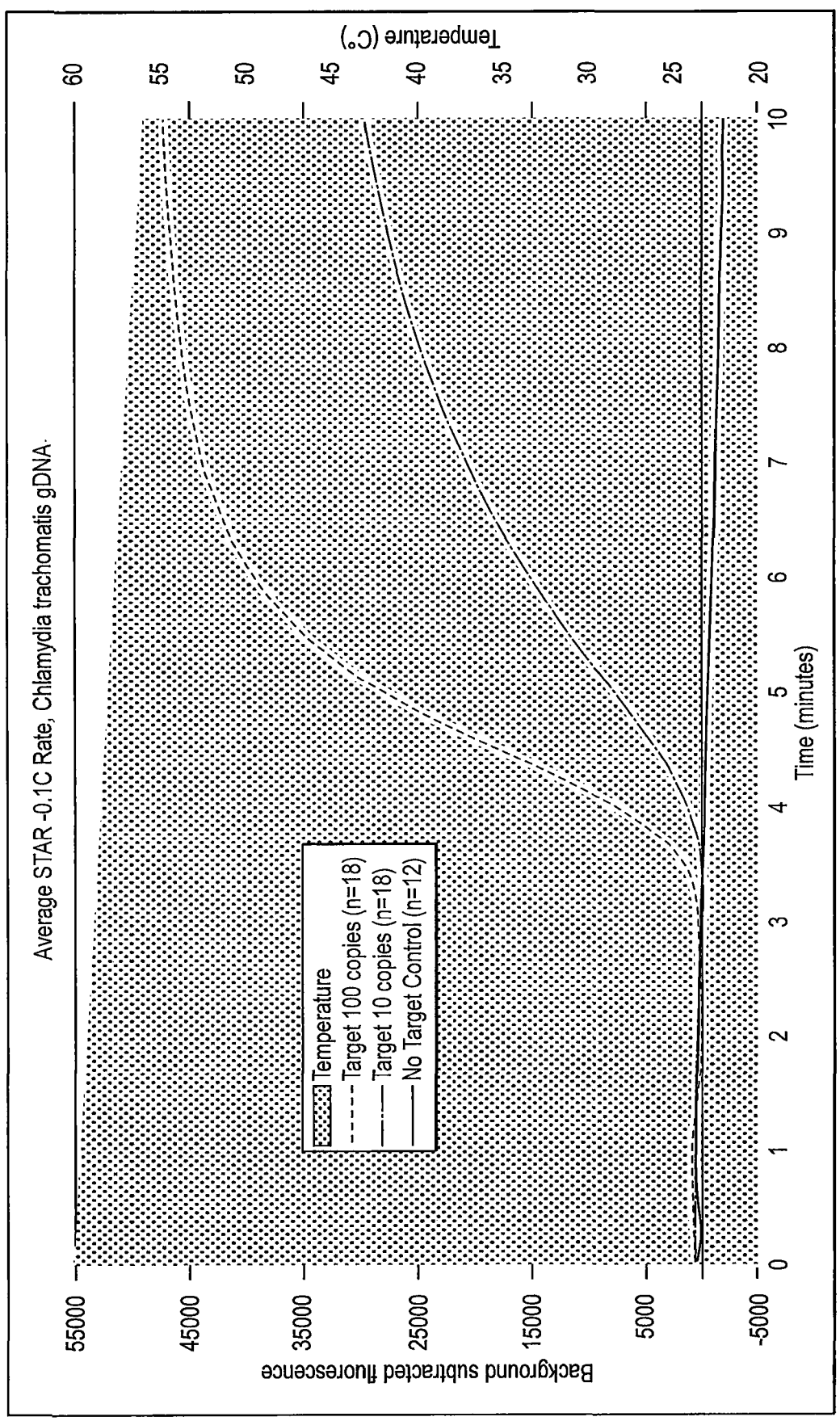
Figure 7:
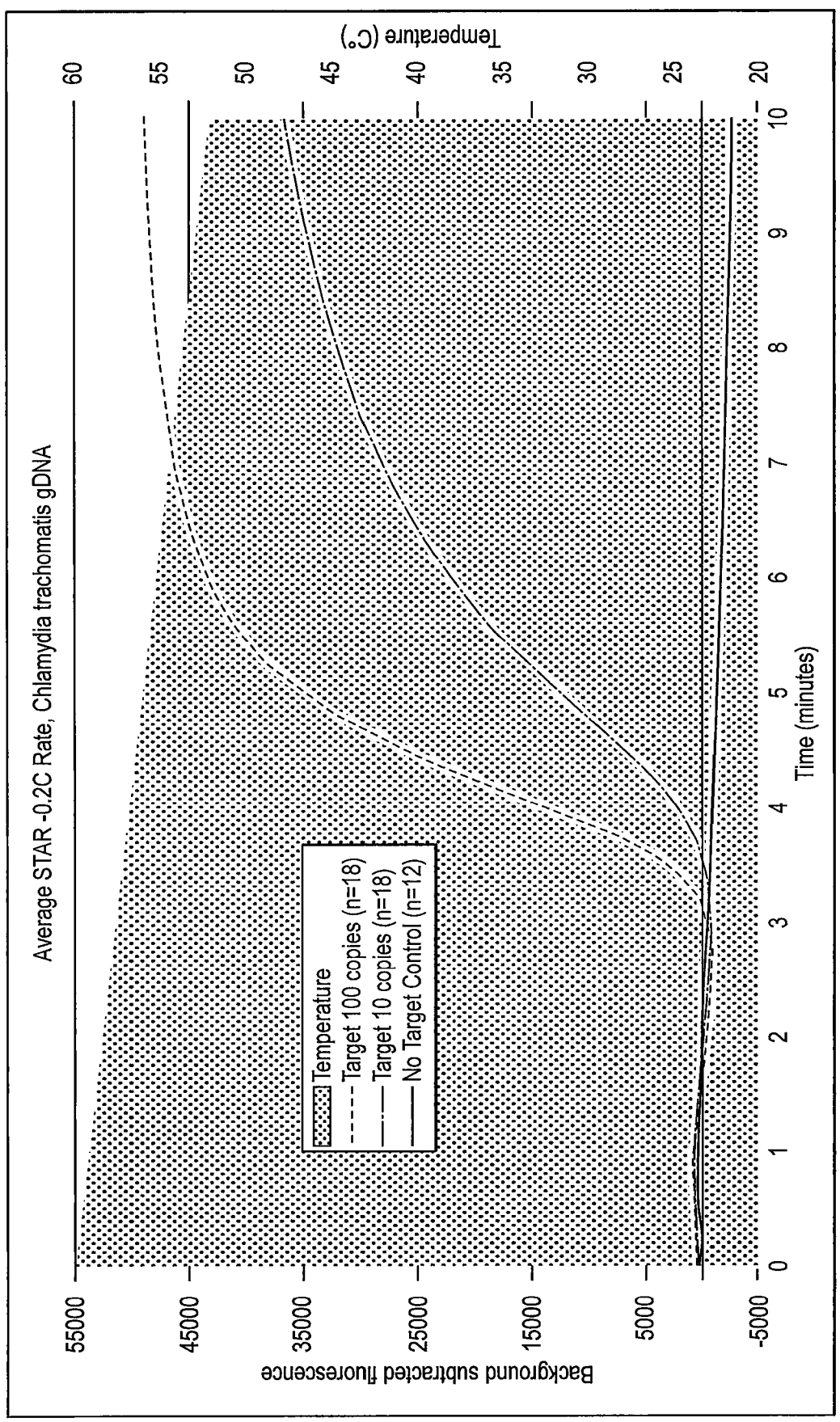
Figure 8:
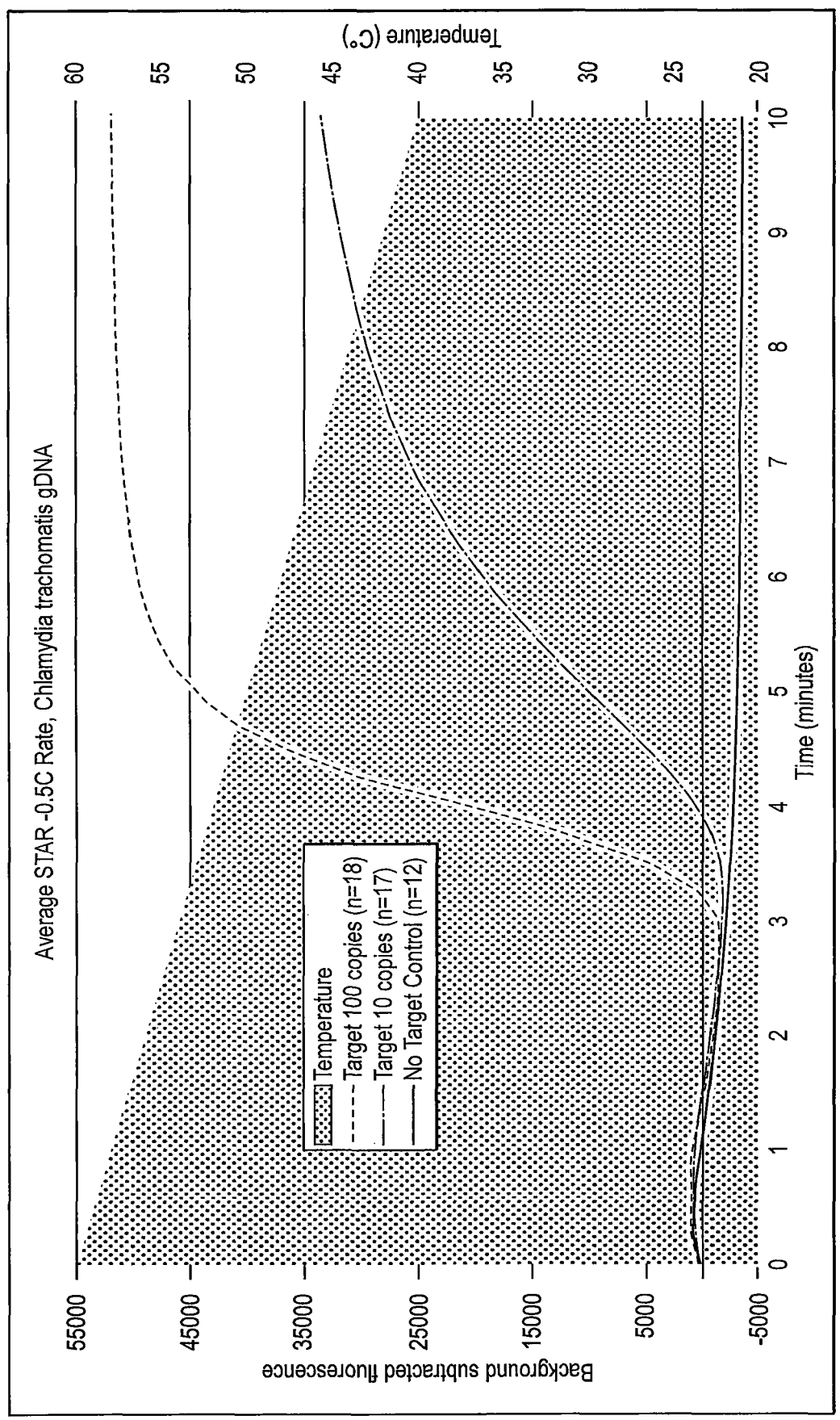
Figure 9:
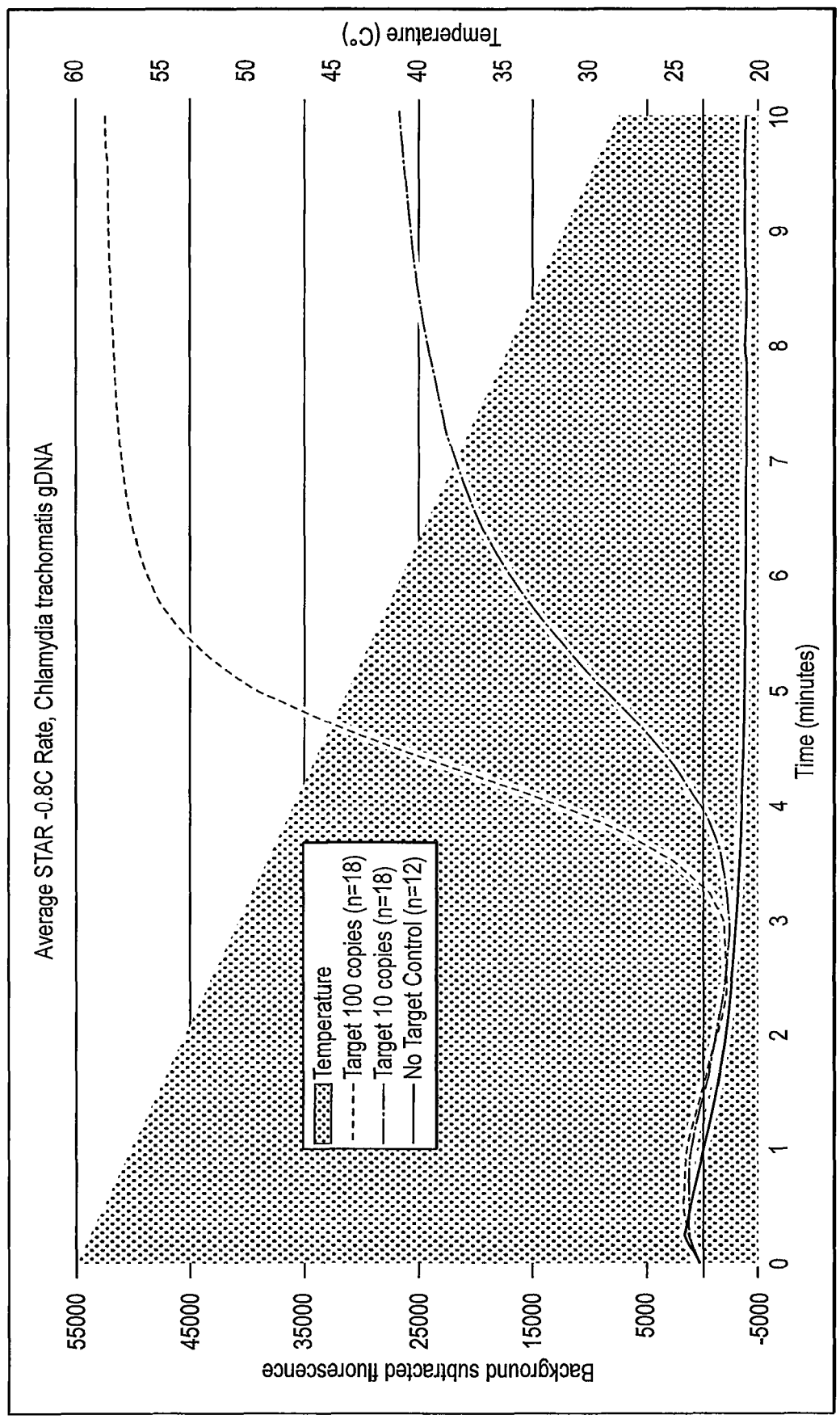
Figure 10:
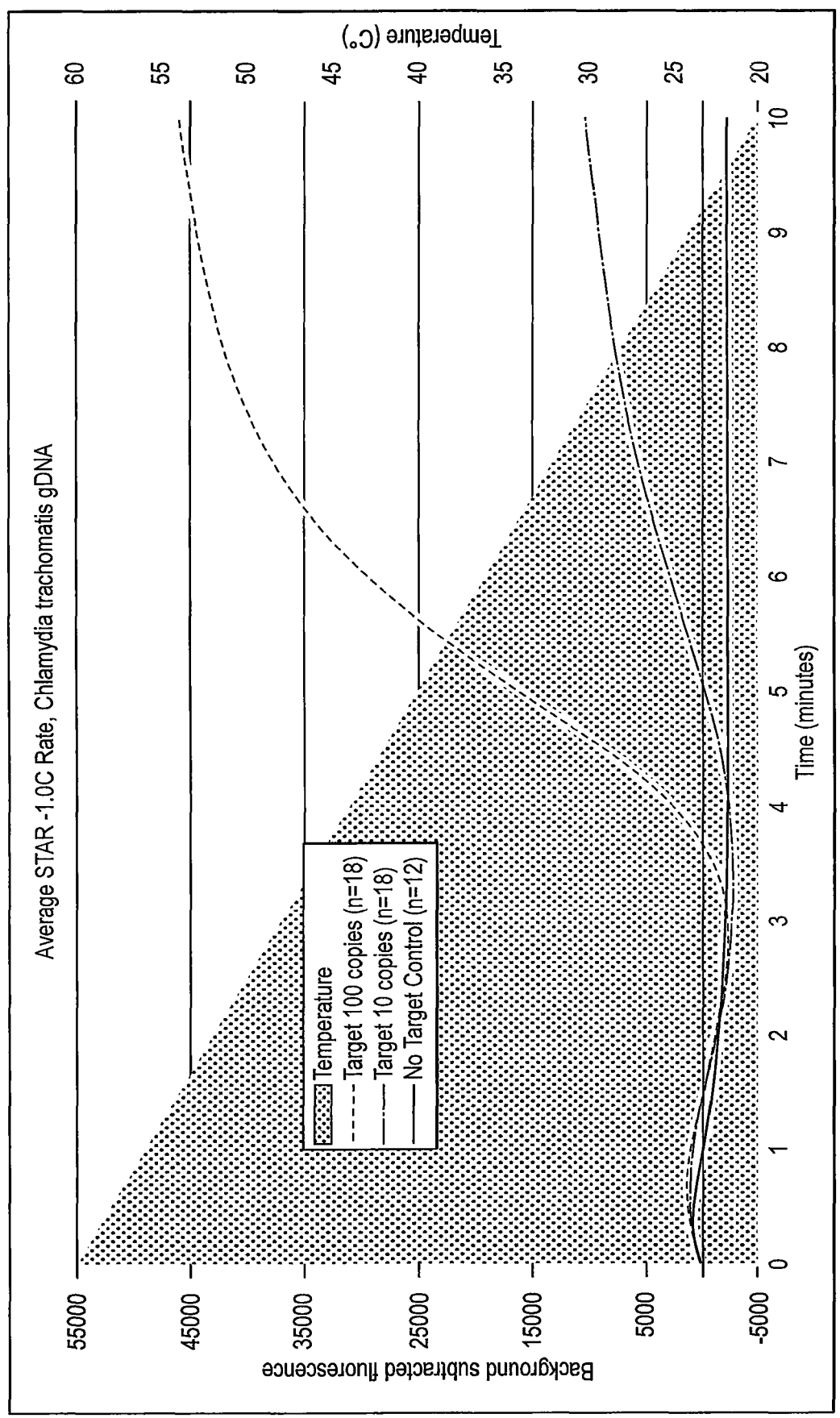

FIGS. 3, 4 and 5 show the results for isothermal amplifications (i.e. not according to the method of the invention) at 50, 56 and 60° C. respectively. As can be seen in FIG. 3, there was essentially no specific amplification at 50° C., strong amplifications at 56° C. (FIG. 4), at least for 100 target copy number, and low amplification at 60° C. (FIG. 5).

FIGS. 6-10 show the results obtained for non-isothermal (STAR) amplification reactions in accordance with the invention, in which the temperature was reduced during the amplification. The rate of temperature reduction was linear, ranging from −0.1° C. per 15 seconds (i.e. −0.4° C. per minute) in FIG. 6, to −1.0° C. per 15 seconds (i.e. −4.0° C. per minute) in FIG. 10. It can be seen that, in all instances, the reactions with 100 copies of target generated more fluorescence signal than the reactions with 10 copies of target, as would be expected. More significantly, the reactions produced much more signal than the equivalent isothermal amplifications, especially for the 10 target copy number reactions. In addition, detectable signal was produced more quickly than in the equivalent isothermal reactions.

Figure 11:
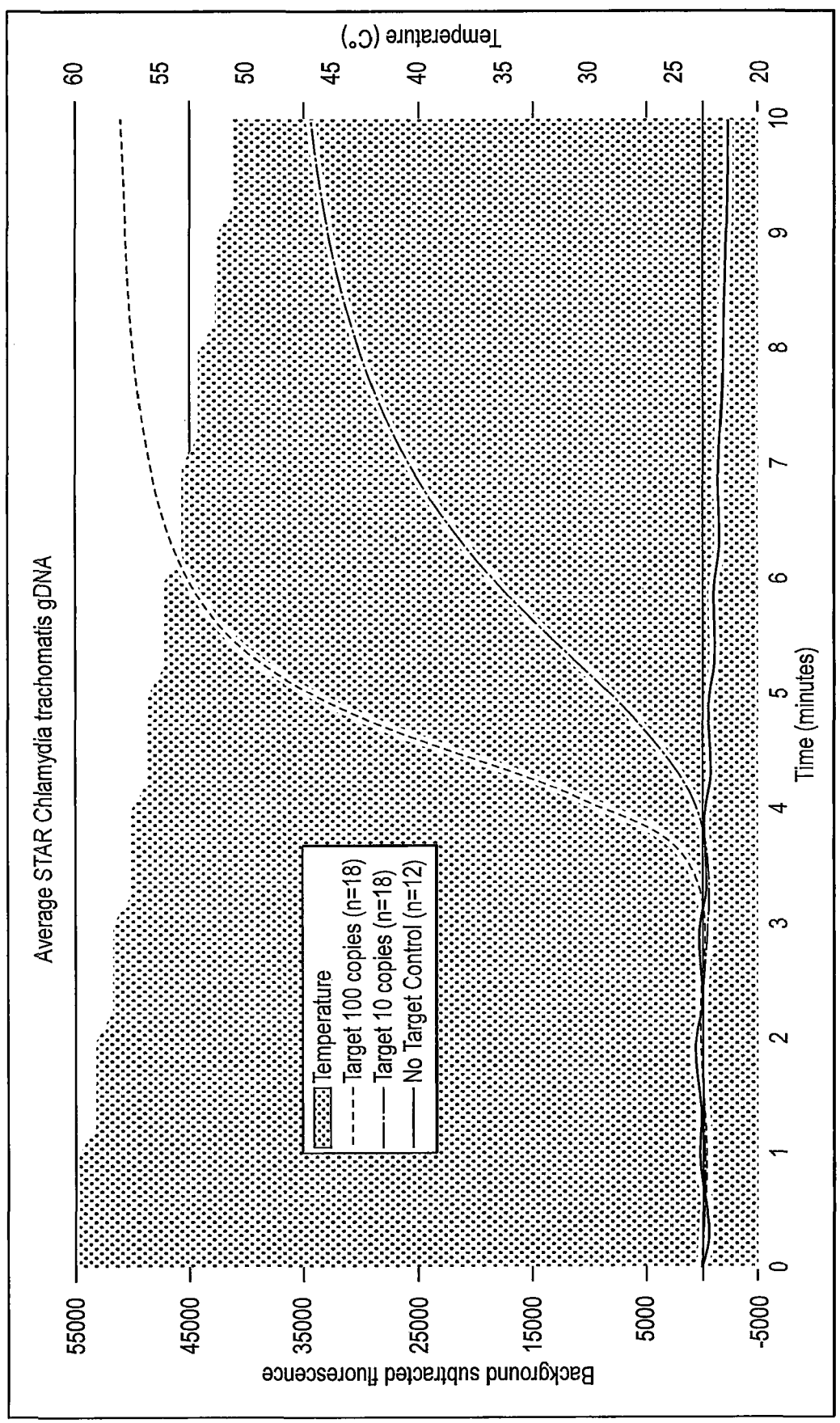

Similar results were obtained when the method of the invention was performed using a non-linear, stepwise temperature reduction (as shown in FIG. 11).

The inventors also found (data omitted for brevity) that the variation in amount of signal between different replicates in STAR reactions was far lower than that between replicates in isothermal reactions, proving that the method of the invention generated much more consistent results. The following comments offer a possible mechanism by which the method of the invention might confer the advantages noted above.

In most nucleic acid amplification reactions primer dimers eventually form, competing for limited reagents and at low target concentrations primer dimers may become the primary amplification pathway for a reaction. Limiting or delaying the formation of primer dimers, even by a small amount, provides significant benefits to a reaction. Because of the rapid nature of the amplification reaction, delaying primer dimer formation allows for preferred amplification pathways to be favoured (i.e. template generation) improving all aspects of amplification. By initiating reactions at elevated temperatures these template pathways become favoured and even preferred. This is seen by the improved sensitivity in the STAR method, improved fluorescence signal, tighter grouping of replicates (i.e. greater reproducibility) and increased speed.

After the initiation phase of the reaction the exponential phase begins. Since the template pathway has been favoured over errant pathways it is desirable to generate as much product as quickly as possible, and this is facilitated by STAR. One of the most likely limiting steps to this generation is the nicking of the sites by the nicking endonuclease. As the temperature of the reaction mix is reduced, it approaches the most favourable temperature for the nicking endonuclease, and the reaction efficiency is increased, generating as much template as possible for detection.

As the temperature decreases further molecular beacons favour template detection and decreased fluorescence background. The melting temperature of the templates to the molecular beacons becomes significantly higher than the detection temperature, generating improved signal as less templates melt from the molecular beacon. Furthermore, due to the decreased temperature, stem melting temperatures become higher than reaction temperatures. Thus the molecular beacon favours a closed phase when no template is present, generating less background signal.

The novel non-isothermal reaction method of the invention provides a substantial improvement over existing isothermal and thermal cycling conditions. By favouring enzyme activity and optimal reaction kinetics the method has improved the change in $A_T$, increased the total amount of fluorescence generated, improved the consistency of amplification and increased the sensitivity of detection.

Example 3: Results Using SYBR® Green II

Because molecular beacons only measure an increase in the total amount of specific single-stranded DNA product, non-specific amplification product is not measured independently of the intended amplification product. To measure the production of non-specific amplification products (e.g. arising from primer dimer formation), separate reactions were carried out in the presence of SYBR® Green II. SYBR® Green II is one of the most sensitives dyes known for detecting single-stranded DNA, RNA, and double-stranded DNA. Because SYBR® Green II has a low intrinsic fluorescence, it is a natural choice for detection of total amplification in a reaction or non-specific amplification if the amplification is done in the presence of no target. The reactions were carried out directly under two conditions, isothermal and non-isothermal (STAR) as displayed below in Table 2.

TABLE 2

| Preincubation | Start | Temperature Decrease | Finish |
|---|---|---|---|
| Isothermal Conditions | | | |
| 56° C. | 56° C. | none | 56° C. |
| STAR Conditions | | | |
| 60° C. | 60° C. | −1.0° C. per minute | 51° C. |

Further, the reactions compared 50 copies of genomic DNA versus no target. SYBR® Green II was acquired at a 10,000× concentration, 0.5× was used per reaction (Life Technologies, Carlsbad). A higher TL, 9000, was used to calculate the $A_T$ due to the intrinsic nature of intercalating dyes. SYBR® Green II has an inverse relationship of fluorescence to temperature. The lower the temperature the higher the fluorescent signal, as described in "Comparison of multiple DNA dyes for real-time PCR: effects of dye concentration and sequence composition on DNA amplification and melting temperature" (Gudnason et al., 2007 Nucl. Acids Res. 35 (19) e 127). The results are shown in Table 3 below.

TABLE 3

| SYBR® Green II Reactions | | |
|---|---|---|
| Target | Average $A_T$ (minutes) | Difference between Target to No Target Amplification |
| Isothermal Conditions | | |
| 50 copies gDNA | 3.75 | 0.25 |
| No Target | 4 | |
| STAR Conditions | | |
| 50 copies gDNA | 3 | 1 |
| No Target | 4 | |

The STAR method exhibits multiple improvements; first it reduces background production which is evident by the longer time it takes for the "no target" to show SYBR® Green II amplification relative to target signal. Secondly, it has improved product amplification, seen by the faster amplification time when target is present. Combined, these improvements more than quadruple the difference between the $A_T$ relative to isothermal methods.

It should be noted that $A_T$ values from isothermal reactions had more variability than $A_T$ values from STAR. This shows the benefit that the new method has in controlling the amplification process and reflects the unpredictability of non-specific amplification pathways using traditional methods.

Example 4: Results Using 2' O-Methyl Modified Primers

As described in U.S. Pat. Nos. 6,794,142 and 6,130,038, the use of 2' O-methyl modified primers are known to reduce primer dimer formation during amplification. US 2005-0059003 describes the use of 2' O-methyl modifications located at the 3' of SDA primers, thus Bst DNA Polymerase I and derivatives can efficiently utilize 2'-modified ribonucleotides as primers for DNA synthesis. Target specific primer regions comprising one or more 2' modified nucleotides (e.g., 2'-O-methyl, 2'-methoxyethoxy, 2'-fluoro, 2'-allyl, 2'-O-[2(methylamino)-2-oxoethyl], 2'-hydroxyl (RNA), 4'-thio, 4'-CH3-O-2'-bridge, 4'-(CH3) 3-O-2'-bridge, 2'-LNA, and 2. —O—(N-methylcarbamate 2'-Suc-OH)) should improve isothermal reactions. If 2' modified nucleotides fully eliminated primer dimer formation it would be surprising that the STAR method could further improve amplification. The reactions were carried out directly between two conditions, isothermal and non-isothermal (STAR) as displayed below.

TABLE 4

| preincubation | Start | Temperature Decrease | Finish |
|---|---|---|---|
| | Isothermal Conditions | | |
| 56° C. | 56° C. | none | 56° C. |
| | STAR Conditions | | |
| 60° C. | 60° C. | −1.0° C. per minute | 51° C. |

The results of amplification using 2' modified nucleotides on the 3' end of primers are shown in table 5 below. Reactions were carried out with a minimum of six replicates in no target reactions and twelve replicates with target reactions.

TABLE 5

SYBR ® Green II Reactions 2' O-methyl modifications

| Target | Average $A_T$ (minutes) | Difference between Target to No Target Amplification |
|---|---|---|
| | Isothermal Conditions | |
| 50 copies gDNA | 5 | 0.5 |
| No Target | 5.75 | |
| | STAR Conditions | |
| 50 copies gDNA | 4 | 1.5 |
| No Target | 5.5 | |

The data demonstrate that the use of at least one primer incorporating 2' O-methyl nucleotides delays the formation of primer dimers improving the reaction, albeit slowing it down. Further, the use of the STAR method not only improved the use of 2' O-methyl amplification, recovering some of the lost speed, but also improved the difference between target to no target amplification by three fold. This indicates that although 2' O-methyl modifications do reduce the production of non-specific, errant, amplification they do not eliminate it. The data further suggest that the STAR method better utilizes the improvements generated by 2' O-methyl modifications than existing techniques previously disclosed.

Without limiting the invention to any particular theory, the potential improvements obtained by using one or more 2' modified nucleotide in the primer region are hypothesized to be largely due to enhancements in the initiation phase of amplification.

During the initial extension of the primer region on a target the incorporation of one or more 2' modified nucleotides in the primer region of STAR causes these nucleotides to be unsuitable to serve as template for polymerase extension in nonspecific complexes formed by interactions of primers, reducing the background signal. It is quite possible that the polymerase stalls as the nucleotide enters the binding pocket. In non-productive reactions (i.e., off-target or primer dimer formation), the stalling effect is sufficient in minimizing aberrant extension because template binding is near its melting temperature. Consequently, 2' modifications are able to restrict undesirable amplification pathways because the reaction has mired. However, during favourable amplifications, 2' modifications reduce melting temperatures thus negatively affecting amplification, slowing down time to amplification. STAR is able to take advantage of 2' modifications while minimizing the negative target amplification drawbacks.

This polymerase stalling further explains why STAR in conjunction with 2' O-methyl modifications improve each other. The initial increase in temperature found in the STAR to method, besides naturally reducing primer dimers, exacerbates the 2' modification stalling and melting of primers before errant amplification can occur, thus both methods complement one another. Furthermore, since STAR involves reducing temperature, the decreases in melting temperature caused by 2' modifications in the primers can be minimized as the reaction proceeds.

Example 5: Results Using Multiple Polymerases

Existing amplification technologies either thermally cycle or run at constant temperature. The method of the present invention does neither but rather runs by decreasing the temperature without cycling. A particular novel feature of the invention is the ability to use enzymes of similar function but with different temperature optima. For example, this technology will allow for the use of multiple primers designed for nicking endonucleases that function at different temperature optima, along with different strand displacement polymerases with different optima. Without limiting the invention to any particular theory, this method opens up rapid amplification methods, allowing for new combinations of enzymes and primers not seen in existing technologies. The reactions below (Table 6) were carried out directly between three conditions, isothermal, non-isothermal (STAR), and non-isothermal (STAR) with BSU polymerase (in addition to the initial MANTA™ 1.0 polymerase) as displayed below. BSU Polymerase was purchased from New England BioLabs (Ipswich, Mass.) and ran at 0.5 U per reaction. All conditions were run using 18 target replicates and 6 no target replicates.

TABLE 6

| preincubation | Start | Temperature Decrease | Finish |
|---|---|---|---|
| | Isothermal Condition | | |
| 56° C. | 56° C. | none | 56° C. |
| | STAR Condition | | |
| 60° C. | 60° C. | −0.5° C. per 15 seconds | 40° C. |
| | STAR Condition + BSU Polymerase | | |
| 60° C. | 60° C. | −0.5° C. per 15 seconds | 40° C. |

Figure 12A:
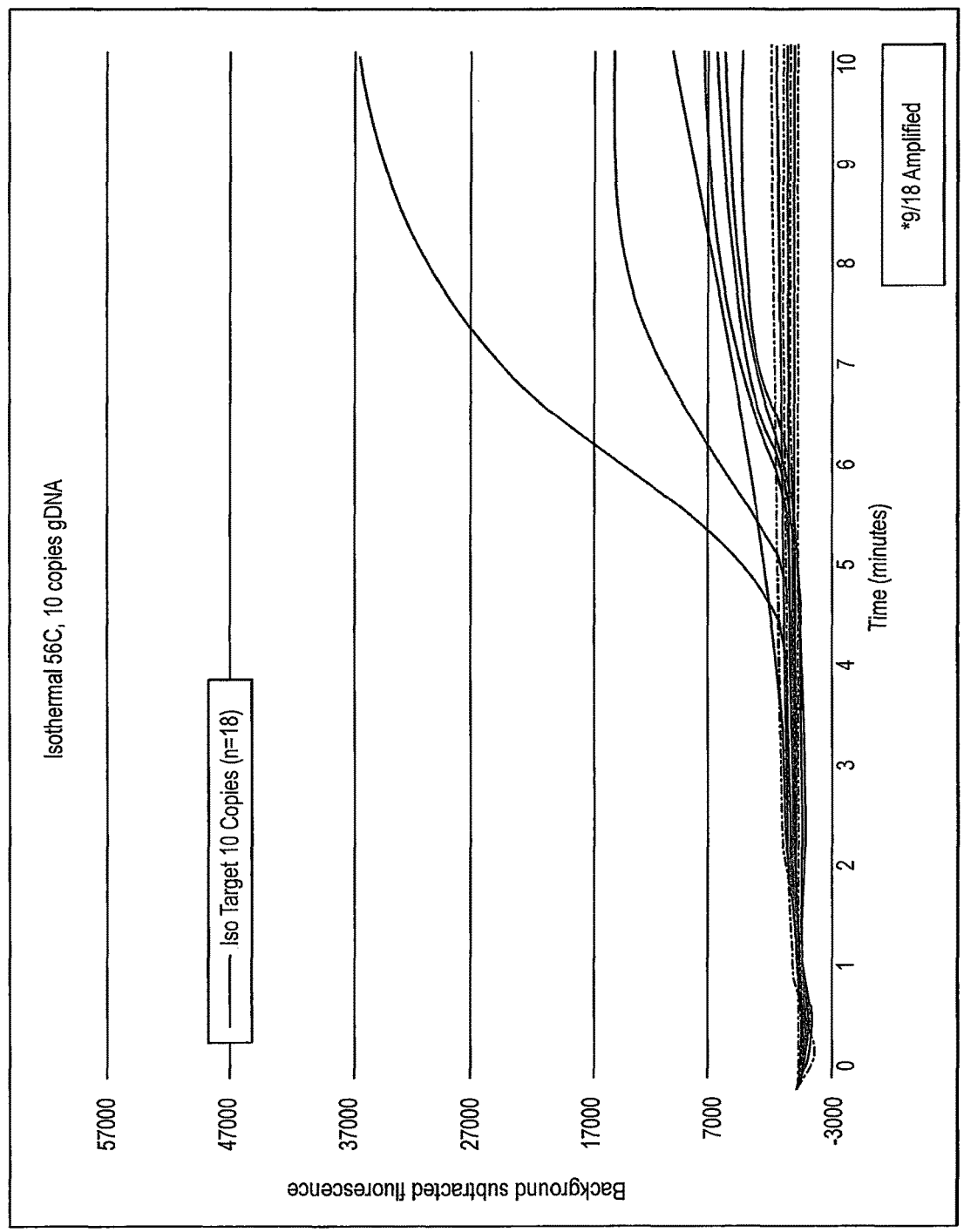
FIGS. 12A-12C are graphs of (background subtracted) fluorescence (arbitrary units) against time for individual replicates of amplification reactions.
Figure 12B:
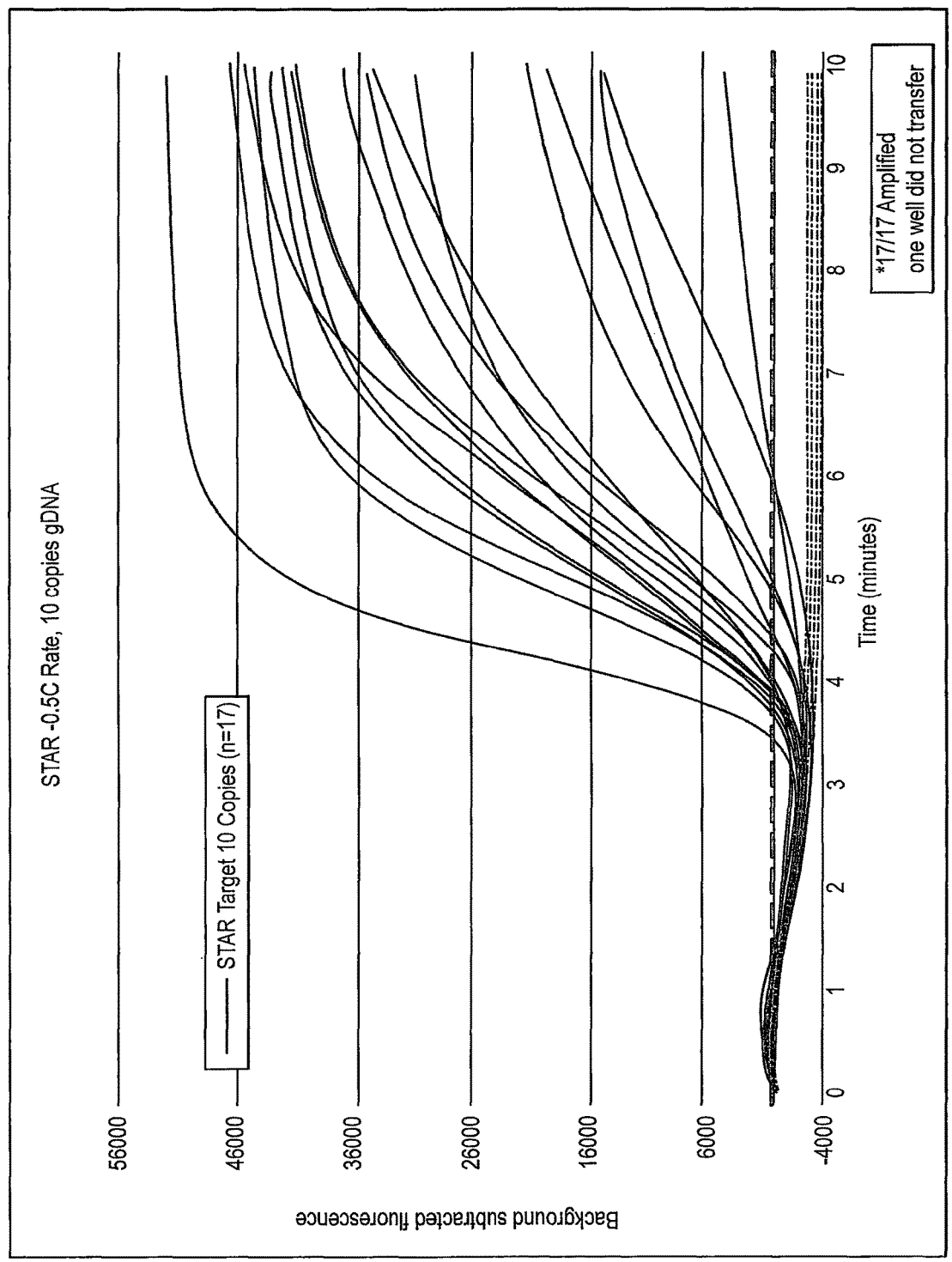
Figure 12C:
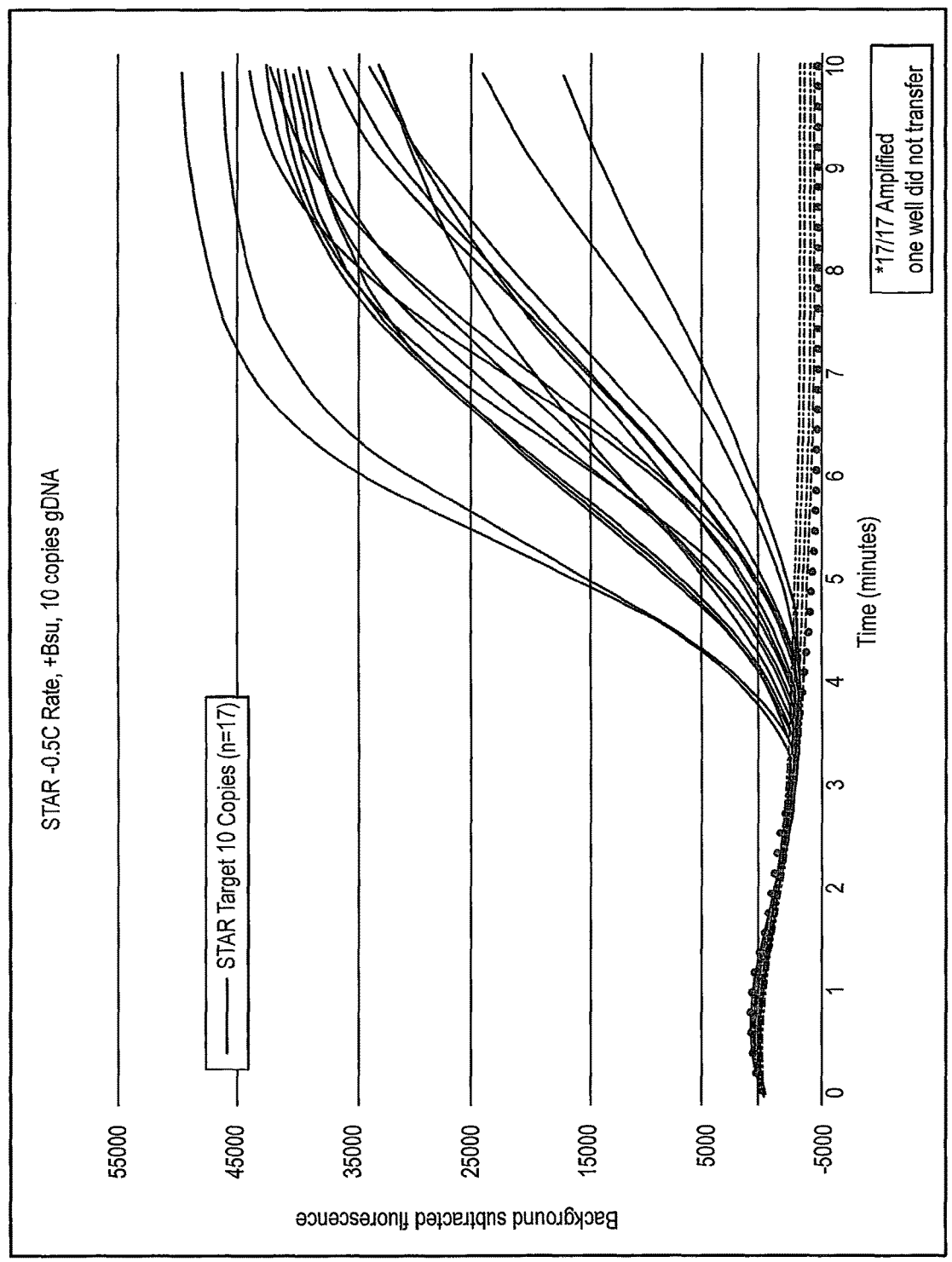

The amplification reactions were performed using samples containing 10 copies of *C. trachomatis* genomic DNA, and the results are shown in FIGS. 12A-12C.

FIG. 12A shows the results for the isothermal reaction (not in accordance with the invention). FIG. 12B shows the results for the STAR reaction in the presence of MANTA™ polymerase alone, and FIG. 12C shows the results for the STAR reaction in the presence of additional BSU polymerase.

The first obvious difference is the lack of detection of 10 copies of genomic DNA by the isothermal method, only 9 of 18 replicates exceeded the fluorescence threshold-level (TL) and could be said to have amplified. Both STAR methods detected 17 of 18 replicates. (It should be noted that the missed replicate in each STAR method was due to a faulty multichannel pipette).

Although the differences between the STAR methods are less stark, the addition of a second polymerase with a lower optimal temperature, 37° C., improved total fluorescence after 10 minutes. Further, the second polymerase also tightens the replicates, decreasing $A_T$ variability. This difference would be further demonstrated if a commercial strand displacement polymerase was available on the market with a temperature optimum at 45° C. to 50° C. The results indicate that the STAR method is superior to the isothermal condition and further that this technology allows for novel new mechanics, enzyme combinations and primer amplification schemes.

Example 6: Reproducibility

Figure 13:
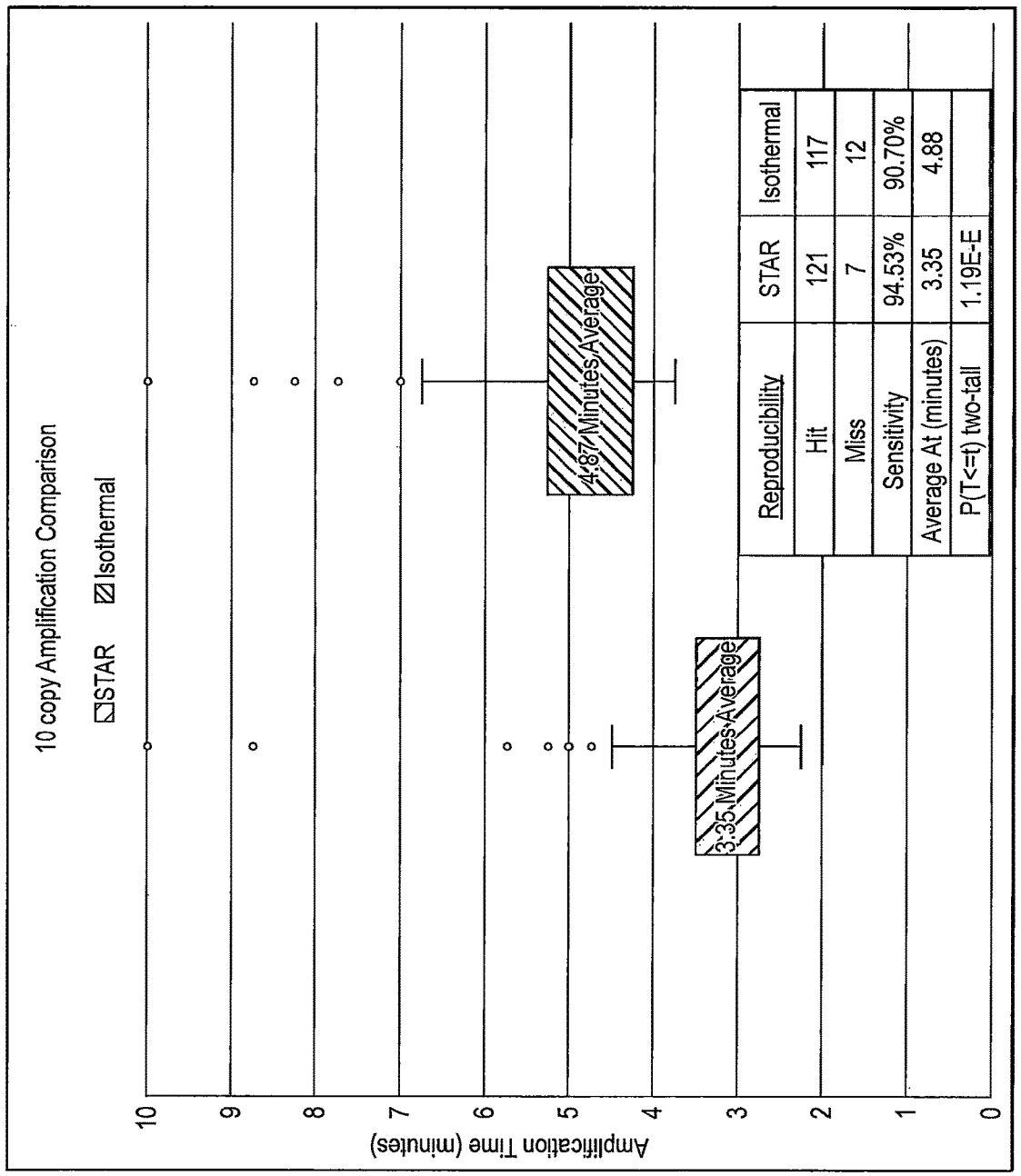
FIG. 13 is a scatter chart comparing the time taken to achieve amplification from 10 copies of template sequence under "STAR" conditions in accordance with the invention or under isothermal conditions.

For validation of the consistency of STAR technology a large replicate study was carried out comparing STAR and published isothermal conditions as described in U.S. Pat. No. 9,562,263. Amplifications, STAR vs Isothermal, were carried out using to 100 plus replicates for reactions containing target and 16 replicates for control reaction mixtures without target. Both conditions used the same buffers, polymerase, nicking enzyme and target. As shown in the scatter plot in FIG. 13, the STAR technology shows a clear improvement in average time ($A_T$) to achieve amplification to threshold level of fluorescence (TL), improved sensitivity, and a reduced standard deviation between replicates. The $A_T$ time for reactions performed according to the invention was 3.35 minutes, whilst the $A_T$ value for reactions performed according to conventional isothermal protocols was 4.88 minutes, a difference which is statistically significant as judged by Two-tailed t-test. Not to limit the applicant to any particular theory, the significant reduction in amplification time is thought to be due to the improved initiation of the reaction, allowing for more efficient low copy amplification, minimized primer dimer events, and increased specific product extensions generate templates faster than previously disclosed methods.

Example 7: Amplification Reactions Performed Beyond Conventional Isothermal Temperature Ranges A further benefit of STAR technology is the ability to amplify outside most common isothermal amplification temperature ranges. As described in U.S. Pat. Nos. 5,712,124, 9,562,263, and 5,399,391, most isothermal amplification technologies have a tight temperature range in which amplification can occur. Outside these typical temperature ranges, conventional isothermal techniques have difficulty amplifying. To demonstrate the versatility of STAR, amplifications were carried out as described in Table 7 below.

TABLE 7

| Isothermal Conditions | | | |
|---|---|---|---|
| preincubation | Start | Temperature Decrease | Finish |
| 63° C. | 63° C. | none | 63° C. |
| 49° C. | 49° C. | none | 49° C. |

| STAR Conditions | | | |
|---|---|---|---|
| preincubation | Start | 1st Temperature Decrease | 1st Stop |
| 62° C. | 62° C. | −0.8° C. per 15 seconds | 32° C. |
| 63° C. | 63° C. | −0.8° C. per 15 seconds | 33° C. |
| 64° C. | 64° C. | −0.9° C. per 15 seconds | 28° C. |

| preincubation | Start | 1$^{st}$ Temperature Decrease | 1$^{st}$ Stop | Drop Immediately restart | 2$^{nd}$ Temperature Decrease | Finish |
|---|---|---|---|---|---|---|
| Two Step STAR Conditions | | | | | | |
| 63° C. | 63° C. | −0.8° C. per 15 seconds | 60° C. | 49° C. | −0.2° C. per 15 seconds | 42° C. |
| One Step STAR then Isothermal Conditions | | | | | | |
| 63° C. | 63° C. | −0.8° C. per 15 seconds | 60° C. | 49° C. | none | 49° C. |

Figure 14A:
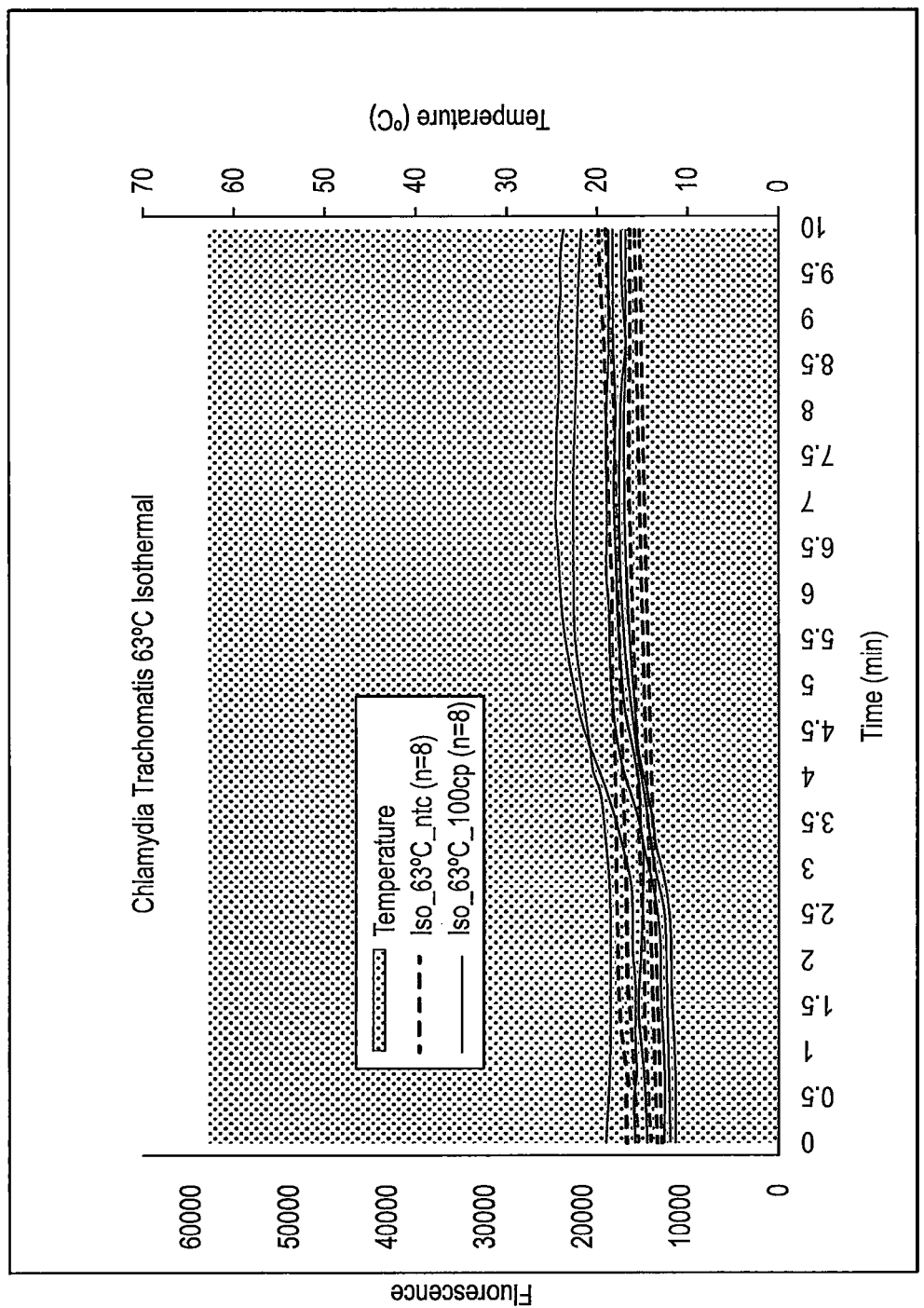
FIGS. 14A and 14B are graphs of (background subtracted) fluorescence (arbitrary units) and temperature (° C.) against time using isothermal amplification conditions (63° C. or 49° C. respectively)
Figure 14B:
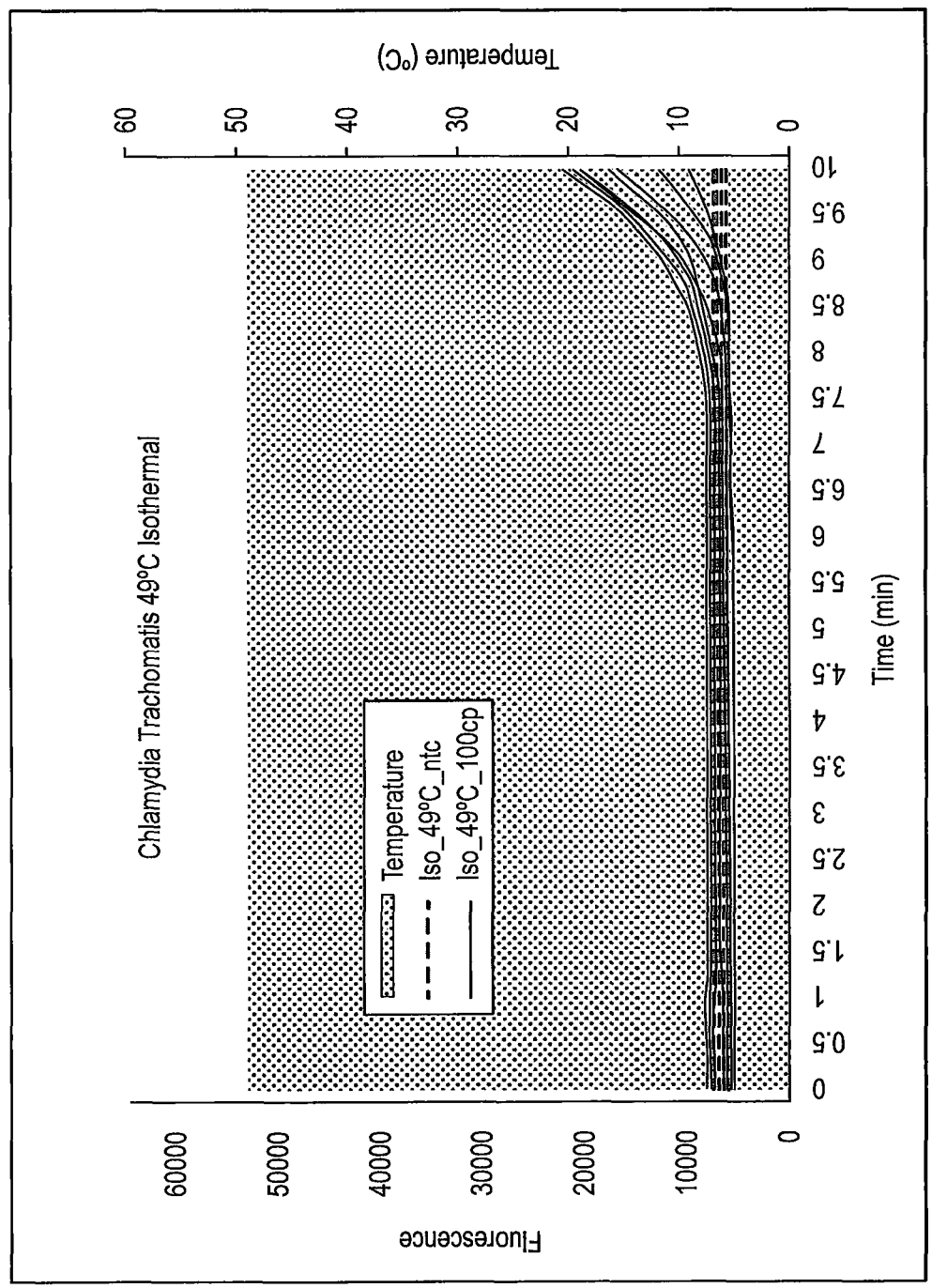

Isothermal reactions were performed as described in U.S. Pat. No. 9,562,263. FIGS. 14A and 14B are graphs showing the amount of fluorescence signal (background subtracted; arbitrary units) against time (minutes) for isothermal amplification reactions performed at either 63° C. (FIG. 14A) or 49° C. (FIG. 14B). In both Figures, the dotted plots represent the results obtained from negative control reactions without template; the solid line plots are the results from the test reactions containing template.

It is clear from FIG. 14A that substantially no template-specific amplification occurs when the reaction temperature is held at 63° C. In FIG. 14B, the results appear to suggest that at 49° C. amplification is occurring from about 9 minutes onwards, but actually this is probably false signal arising from interactions of molecular beacons with primers (data not shown).

Figure 15A:
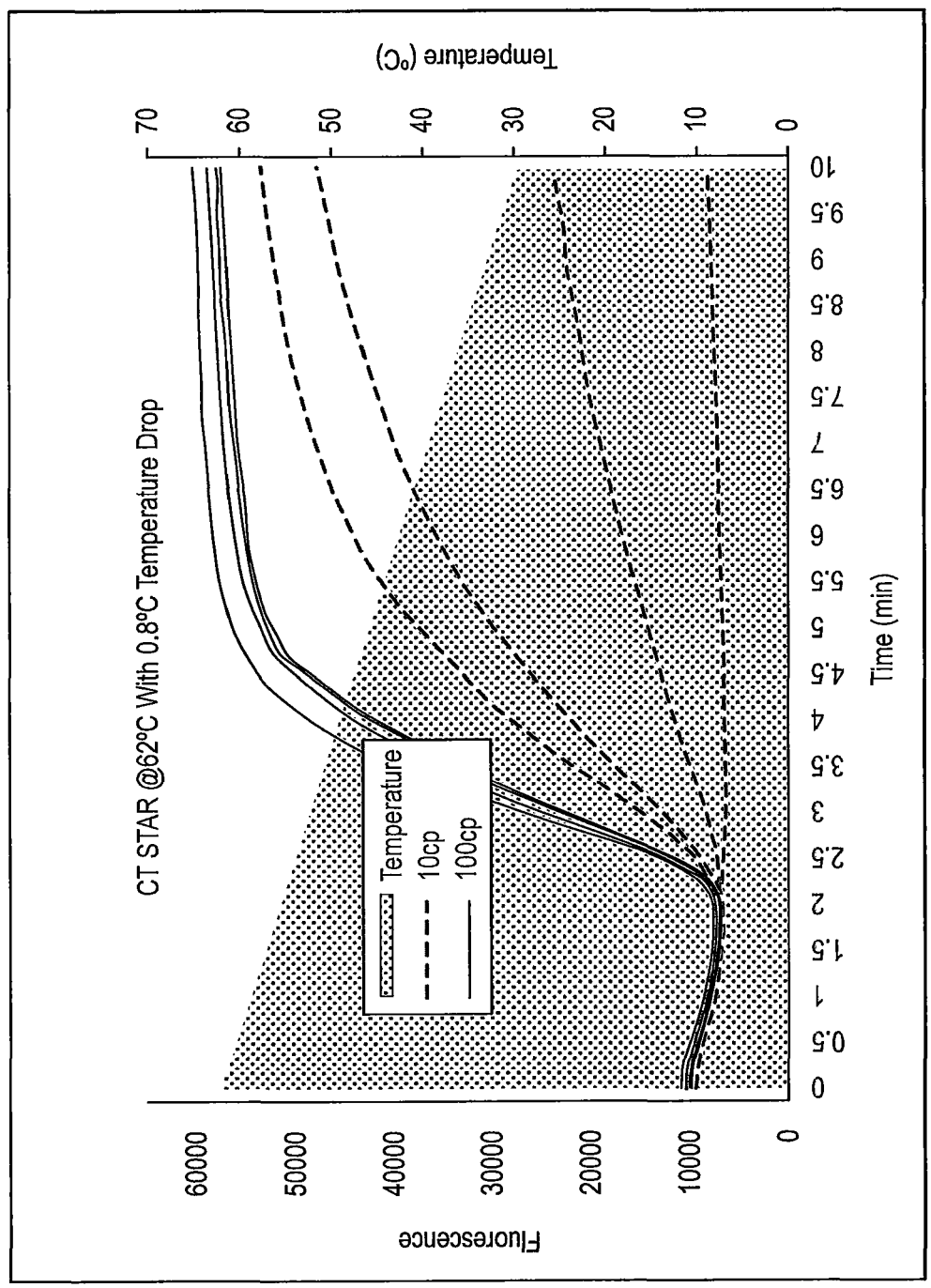
FIGS. 15A, 15B and 15C are graphs of (background subtracted) fluorescence (arbitrary units) and temperature (° C.) against time (minutes) for individual replicates (10 copies or 100 copies; broken and solid lines respectively) for amplification reactions in accordance with the invention under various temperature profiles.
Figure 15B:
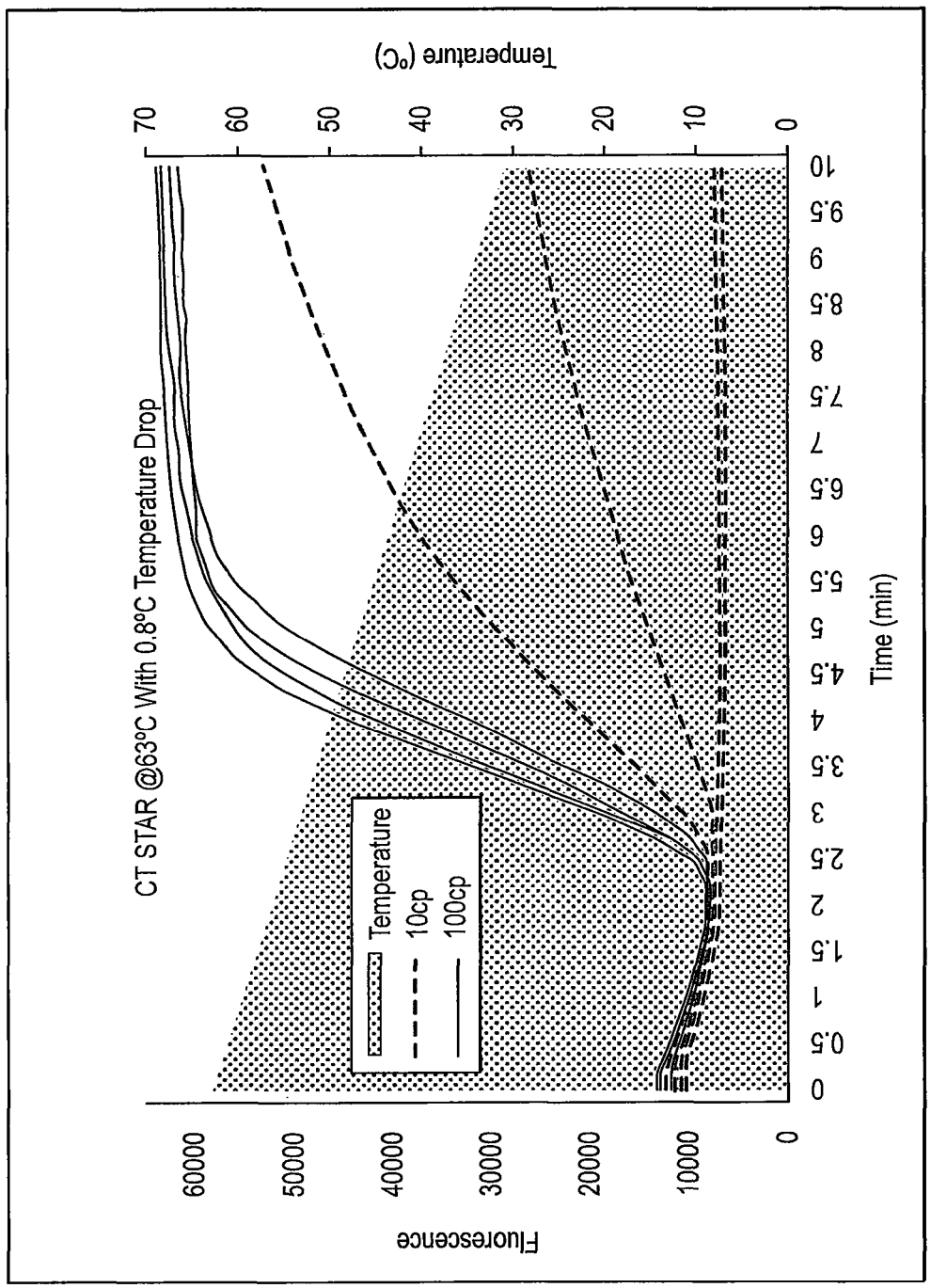
Figure 15C:
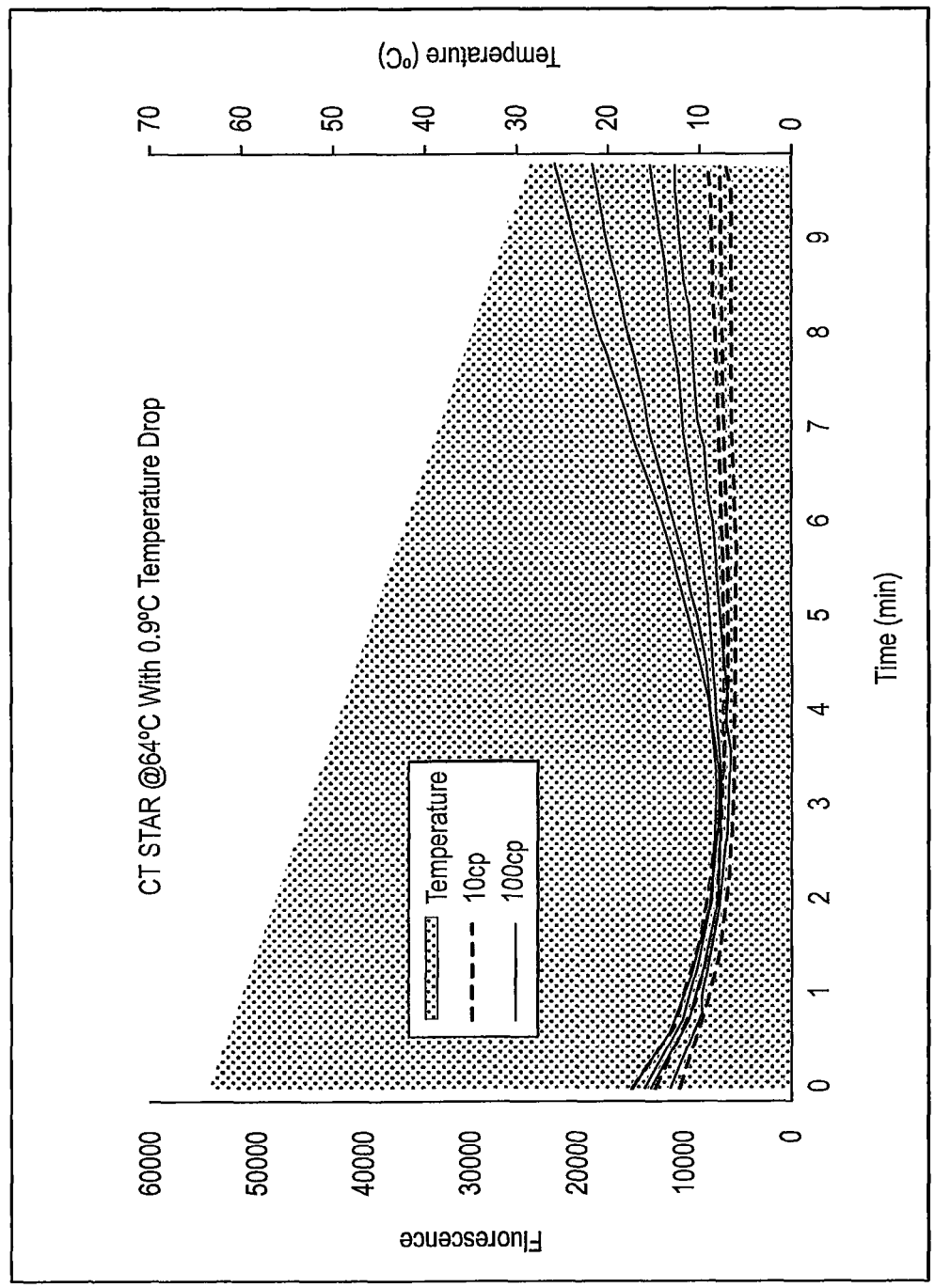

In contrast to the isothermal reactions, "STAR" reactions performed in accordance with the invention could be initiated at elevated temperatures and still achieve good amplification. The results from these reactions are shown in FIGS. 15A, B and C. These are graphs of fluorescence (background subtracted, arbitrary units) against time (minutes). The solid shading indicates the temperature (° C.) during the reactions. The dotted plots represent the results obtained using 10 copies of target, the solid plots represent the results obtained using 100 copies of target. In FIG. 15A, the initial temperature was 62° C., and the rate of temperature decrease was −0.8° C. per 15 seconds (i.e. −3.2° C. per minute). In FIG. 15B, the initial temperature was 63° C., and the rate of temperature decrease was −0.8° C. per 15 seconds. In FIG. 15C, the initial temperature was 64° C., and the rate of temperature decrease was −0.9° C. per 15 seconds (i.e. −3.6° C. per minute). It is apparent from the Figures that an initial temperature of 62 or even 63° C. provides good results for STAR reactions, and there is even some amplification using an initial temperature of 64° C. although this is clearly sub-optimal.

Figure 16A:
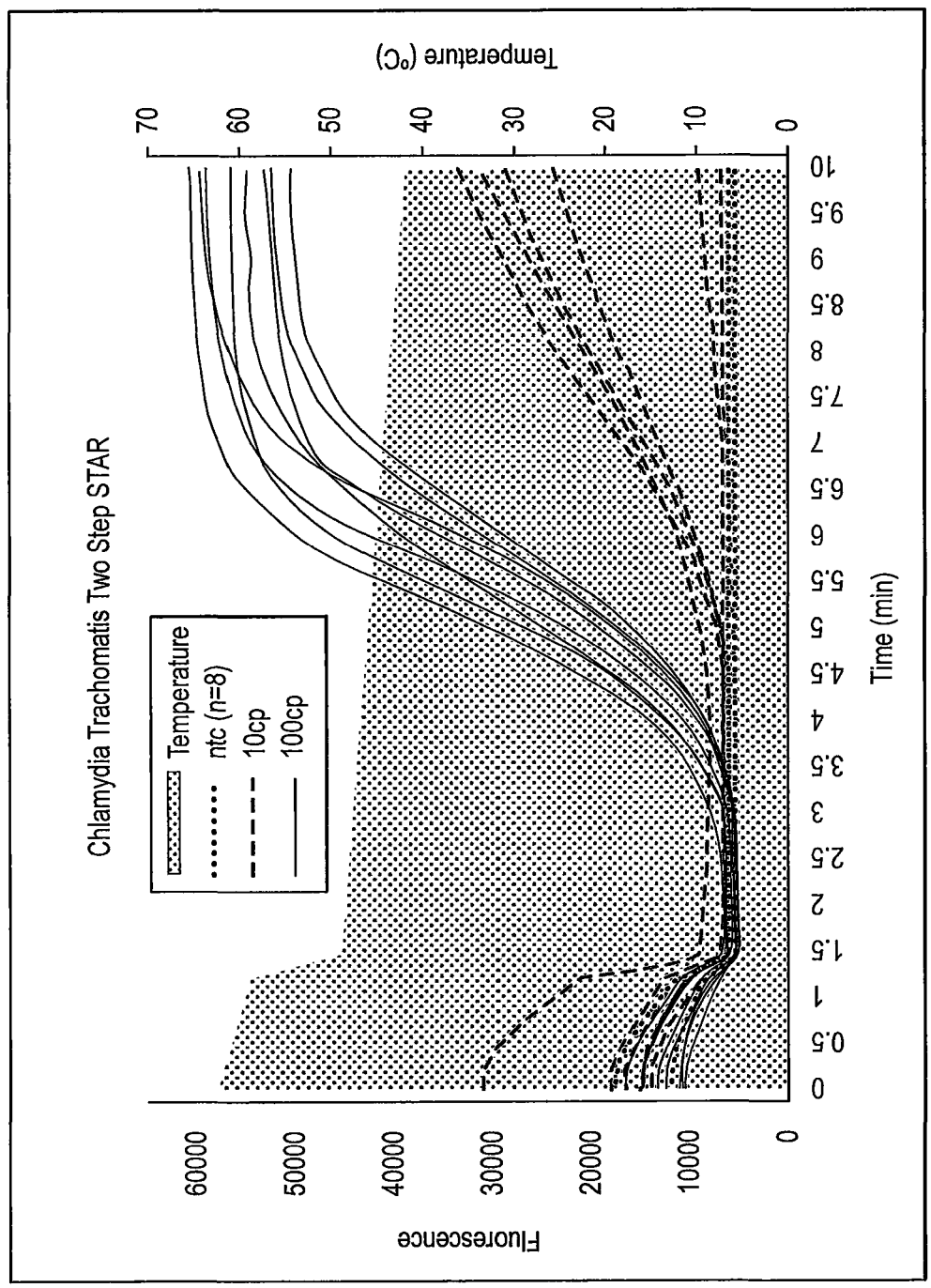
FIGS. 16A and 16B are graphs of (background subtracted) fluorescence (arbitrary units) and temperature against time (minutes) for amplification reactions in accordance with the invention under different temperature profiles.
Figure 16B:
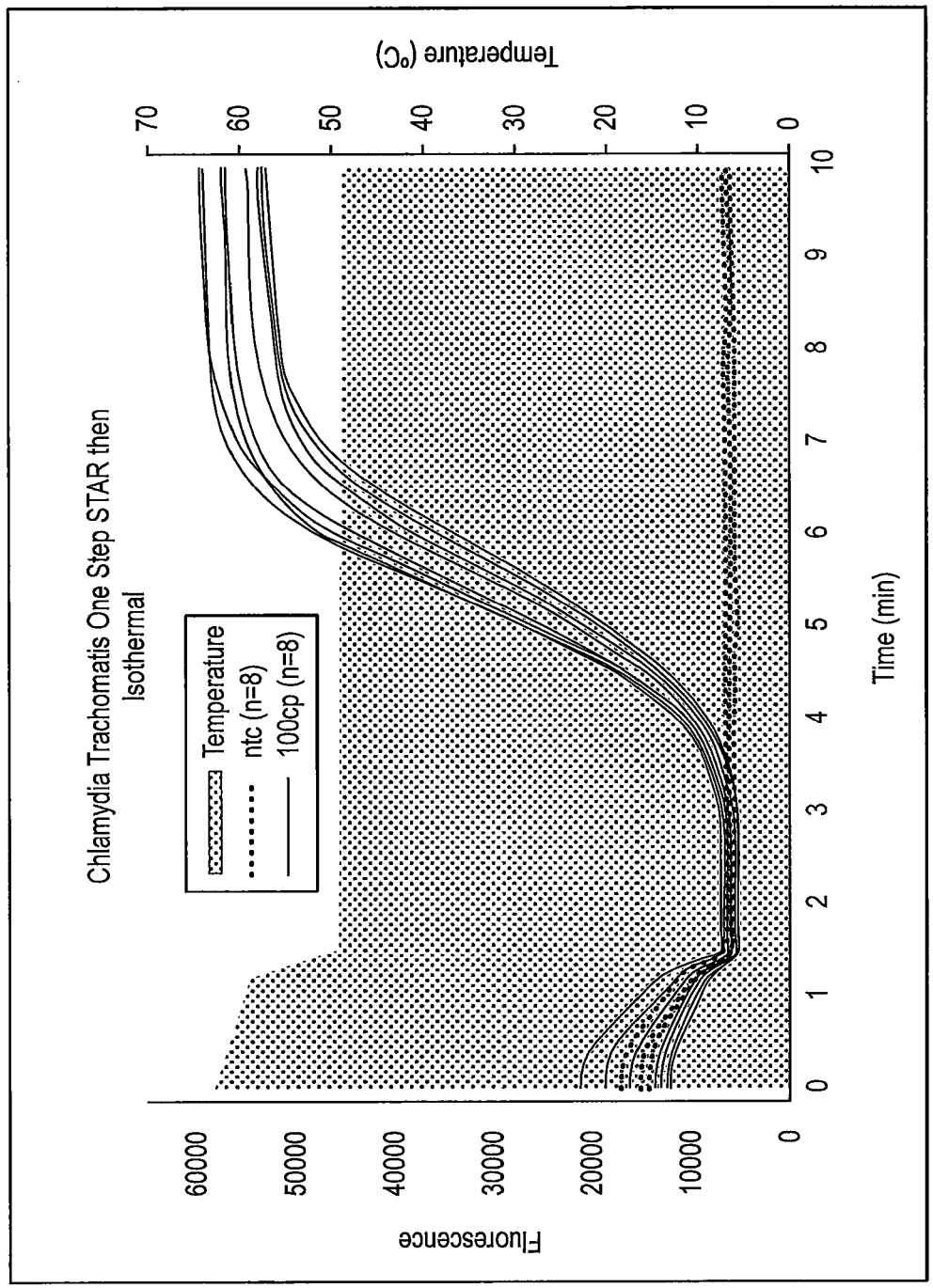

In addition, experiments were performed using large temperature drops. The results are shown in FIGS. 16A and 16B. The graphs show the results for no target negative controls (no fluorescence signal above threshold level) and for STAR reactions performed in the presence of 10 or 100 copies of target C. trachomatis genomic DNA.

FIG. 16A shows the results obtained using an initial temperature of 63° C., followed by a temperature reduction rate of −0.8° C. per 15 seconds for 1 minute, followed by a sudden reduction to 49° C., and then a gradual temperature reduction of −0.2° C. per 15 seconds (i.e. −0.8° C. per minute) for the duration of the reaction. The graph shows that amplification was achieved for both 10 and 100 copy number reactions, although there was approximately twice as much fluorescence signal for the 100 copy target reactions compared to the 10 copy target reactions, and there was considerable intra-group variability.

FIG. 16B shows the results obtained using the same 63° C. initial temperature for 1 minute, followed by the sudden reduction to 49° C. Thereafter, the reaction temperature was held at 49° C. for the duration of the experiment. It can be seen from the graph that there is good specific amplification and much less intra-group variation (reactions performed with 100 copy number target or no target only).

The ability of STAR to amplify across a 40° C. temperature range clearly indicates that STAR is very different from conventional amplification reactions. Atypical reaction temperatures with large ranges are unusual and would not be expected to work. Not to limit the applicant to any particular theory, it is unexpected that these large temperature ranges seem to be less restrictive on amplification for STAR than for conventional amplification methods. Possibly the ability of STAR to achieve superior amplification across a larger range of temperatures is due to improving primer specificity and binding along with strategically utilizing enzyme temperature optima. By utilizing a higher temperature for the initiation phase, one favours true product amplification and thus improves the efficiency of all subsequent phases, exponential amplification and detection. This selection and subsequent temperature drop opens up the amplification toolbox as new schemas for enzymes, primers, and temperatures can be realized.

Example 8: Results using Six- and Seven-2'-O-methyl

Figure 17A:
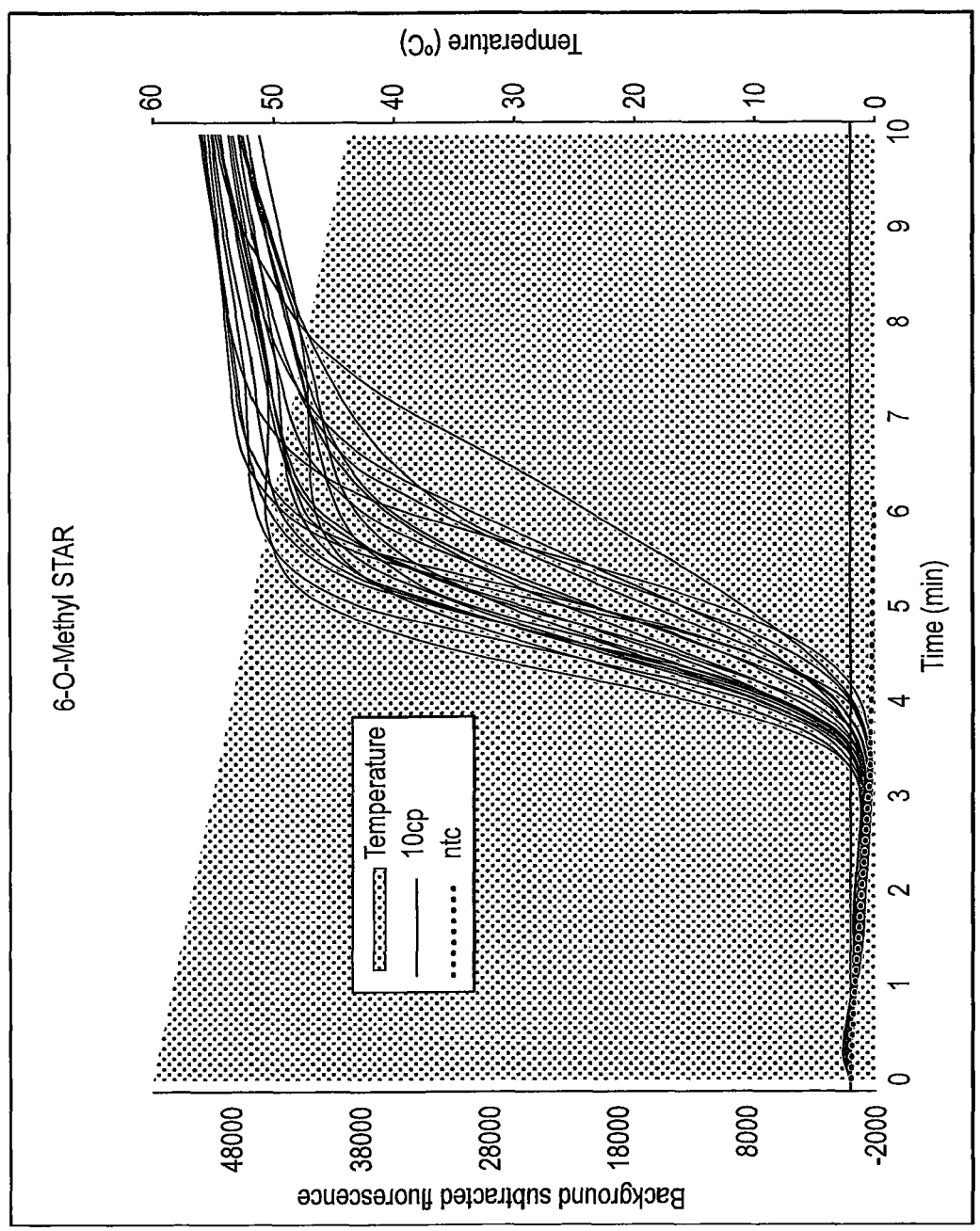
FIGS. 17A and 17B are graphs of (background subtracted) fluorescence (arbitrary units) and temperature (° C.) against time (minutes) for amplification reactions in accordance with the invention performed using primers containing 6 (FIG. 17A) or 7 (FIG. 17B) O-methylated bases.
Figure 17B:
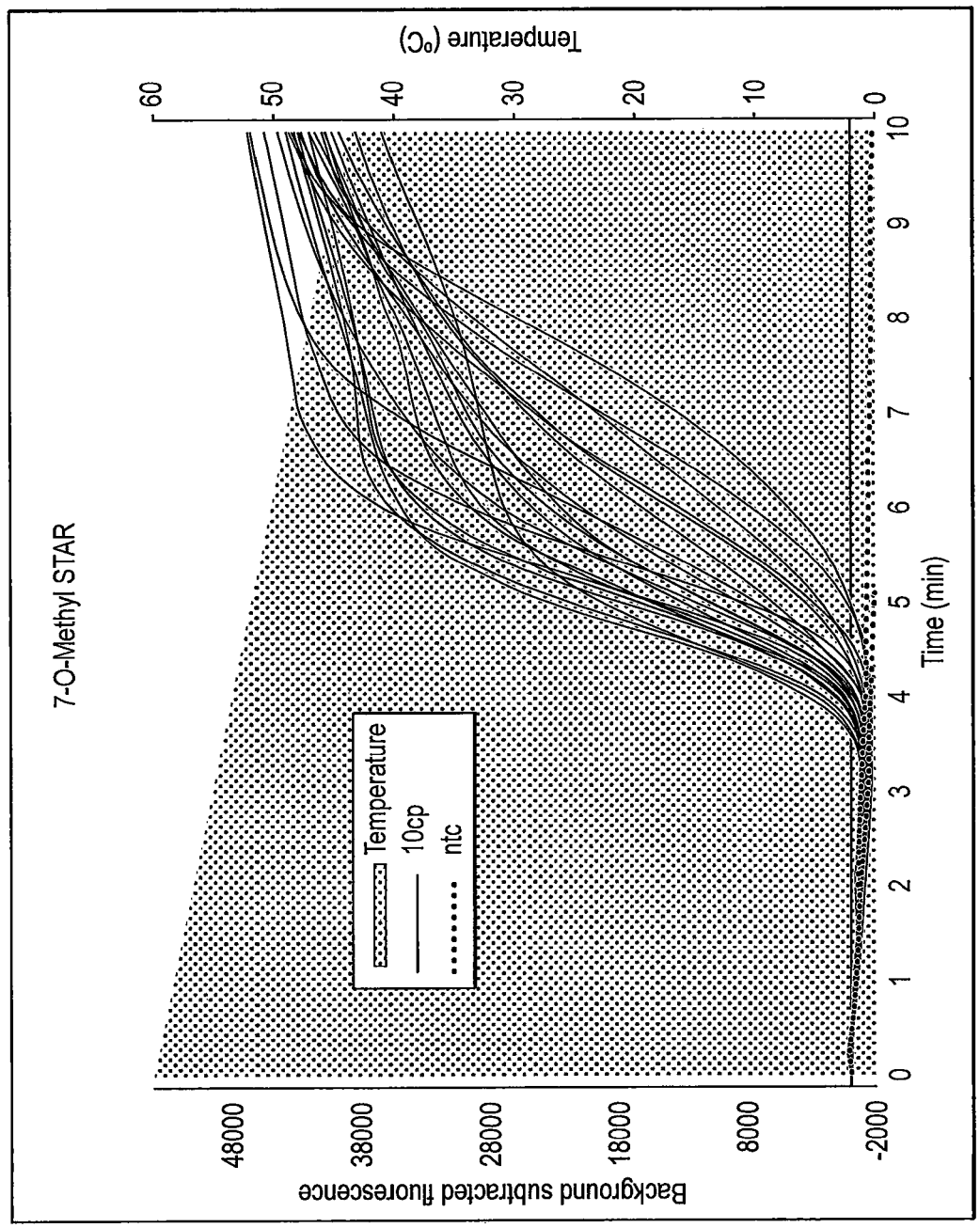

As previously described, 2'-O-methyl modified primers are known to reduce primer dimer formation during amplification. Further illustrating the cooperative nature of these modifications with the STAR technology is the ability to incorporate large strings of 2'-O-methyl modifications and still achieve amplification. Typically, 2'-O-methyl modifications stall the polymerase, permanently retarding amplification; six or more is believed to cause the polymerase to "fall off" the complex rather than just stall. FIGS. 17A and 17B demonstrate STAR's ability to tolerate these modifications and achieve significant amplification with longer 2'-O-methyl strings than previously identified. The structure of the primers containing 2'-O-methylated bases is shown in FIGS. 1B and 1C.

FIGS. 17A and 17B are graphs of (background-subtracted) fluorescence (arbitrary units) against time (minutes). The shading indicates the temperature profile (° C.) over time during the course of the amplification reactions. FIG. 17A shows the results for reactions performed using primers containing 6 2'-O-methyl modified bases, and FIG. 17B shows the results for reactions performed using 7 2'-O-methyl modified bases. In both cases, no target negative control reactions did not generate any fluorescence signal, whereas there was good amplification using either of the modified primers, although the average fluorescence signal was slightly higher for the 6 modified base primers, and the intra-group variation was considerably less compared to the results from the 7 modified base primers.

As seen in the figures, primers containing strings of six and seven 2' O-methyl's amplify well with STAR. This could be due to the ability of STAR to begin amplification in the highly favourable temperature regions of strand displacement polymerases, around 65° C. This favourable region may allow the polymerase to extend longer 2' modified strings allowing for initiation that other technologies lack. For brevity data is not shown but it can also be described that the full length of primer regions have been modified with 2'-O-methyl's and shown amplification, although slower and with lower fluorescent signal.

Example 9: Results Using Ribonucleic Acid

STAR can amplify from any nucleic acid, using any composition of DNA (cDNA and gDNA), RNA (mRNA, tRNA, rRNA, siRNA, microRNA), RNA/DNA analogs, sugar analogs, hybrids, polyamide nucleic acid, and other known analogs. Amplification of ribosomal RNA was carried out as described below.

Enzymes, Oligonucleotides, and Target:

Listeria monocytogenes was used as the target for the development of the STAR RNA assay. Listeria monocytogenes (ATCC VR-886) genomic DNA was acquired from American Type Culture Collection (Manassas, Va.). Initial screening was performed on gDNA, and a 23S region of ribosomal RNA was found to be amplified with primers LMONF72 (SEQ ID NO: 4, 5'-GGACTCGA-TATCGAGTCCAGTTACGATTTGTTG-3') and LMONR86 (SEQ ID NO: 5, 5'-gGACTCCATATG-GAGTCCTACGGCTCCGCTTTT-3'). The resulting DNA template was detected using a molecular beacon LMO-NMB1 (SEQ ID NO: 6, 5'-FAM/gctgcGTTCCAAT-TCGCCTTTTTCGCagc/BHQ1-3') as described in EP No. 0728218. Total RNA was isolated using the RNEASY® Plus mini kit Qiagen (Hilden, Germany) combined with rapid mechanical lysis on a Mini Bead Mill 4 (VWR). Listeria monocytogenes (ATCC BAA-2660) was acquired from American Type Culture Collection (Manassas, Va.), and revived by plating on brain-heart infusion agar plates (BHI). A single colony was used to inoculate 25 mL of BHI media that was grown for 18 hours at 37° C. to reach stationary phase. The culture was then back-diluted and grown for an additional four hours prior to harvest. Bacteria pellets were resuspended in RLT lysis buffer, and homogenised on the Mini Bead Mill (VWR). Total RNA was purified per manufacturer's directions (Qiagen). Genomic DNA was removed by passing lysates over a DNA-binding column provided in the RNEASY® Plus purification kit. Genomic DNA contamination was further minimized by an on-column DNAse I digestion of samples on the RNEASY® RNA-binding column. Bst X DNA Polymerase was purchased from Beverly Qiagen (Beverly, Mass.). OMNISCRIPT®, a Reverse Transcriptase, was purchased from Qiagen (Hilden, Germany). Nt.BstNBI nicking endonuclease was purchased from New England BioLabs (Ipswich, Mass.) as described in U.S. Pat. No. 6,191,267. Oligonucleotides and molecular beacons were synthesized by Integrated DNA Technologies (Coralville, Iowa).

Amplification Conditions:

The basic STAR mixture contained everything as described in example 1 above with the additional inclusion of the following: 4 U of Reverse Transcriptase (referenced above) and replacement of MANTA™ 1.0 for Bst.X.

Figure 18:
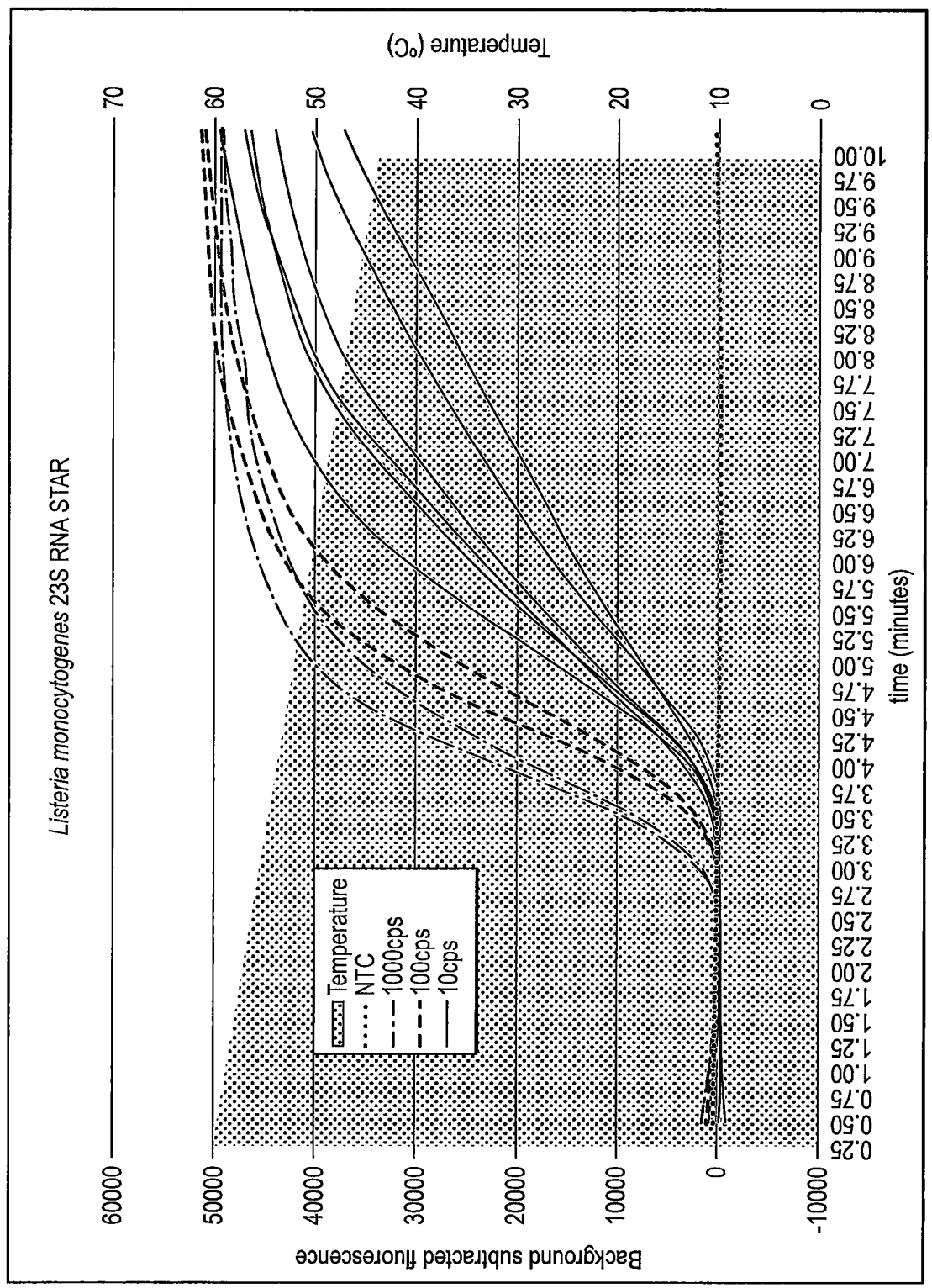
FIG. 18 is a graph of (background subtracted) fluorescence (arbitrary units) against time (minutes) for amplification reactions performed in accordance with the invention using a DNA target generated by reverse transcription of *Listeria monocytogenes* 23S RNA.

The results are shown in FIG. 18 which is a graph of fluorescence (arbitrary units) against time (minutes). The shading denotes the temperature profile during the course of the reaction. Negative control reactions did not generate any fluorescence signal, whereas 10, 100 or 1000 copy number target reactions generated fluorescence signal above threshold in decreasing amounts of time (approximately 3.5 minutes, 3.0 and 2.75 minutes respectively). The results show that STAR could amplify effectively from reverse transcribed RNA target.

The invention claimed is:

1. A method of performing a non-isothermal nucleic acid amplification reaction, the method comprising the steps of:
    (a) mixing a target sequence with one or more complementary single-stranded primers in conditions which permit a hybridisation event in which the primers hybridise to the target, which hybridisation event, directly or indirectly, leads to the formation of a duplex structure comprising two nicking sites disposed at or near opposite ends of the duplex; and performing an amplification process by;
    (b) causing a nick at each of said nicking sites in the strands of the duplex;
    (c) using a polymerase to extend the nicked strands so as to form newly synthesised nucleic acid, wherein extension with the polymerase recreates nicking sites; and
    (d) repeating steps (b) and (c) as desired so as to cause the production of multiple copies of the newly synthesised nucleic acid;
    wherein the temperature at which the method is performed is non-isothermal, and subject to a reduction of at least 2° C. during the amplification process of steps (b)-(d) and wherein the temperature of the reaction does not return to a predetermined temperature.

2. A method according to claim 1, wherein in step (a) the target comprises two complementary strands of nucleic acid, and the method uses forward and reverse primers which are each complementary to a respective strand of the target, such that the 3' ends of the forward and reverse primers are oriented towards each other.

3. The method according to claim 1, wherein the temperature is subject to a controlled reduction of at least 15° C. during the amplification reaction.

4. The method according to claim 1, wherein the average rate of temperature reduction during the amplification reaction is in the range of −0.40 to −3.5° C. min-1.

5. The method according to claim 1, wherein steps (b)-(d) are performed substantially immediately after step (a), and wherein steps (a)-(d) are performed in the same reaction vessel or on the same solid support.

6. The method according to claim 1, wherein step (a) is performed at a temperature in the range of 58-60° C.

7. The method according to claim 1, further comprising the step of detecting, directly or indirectly, the newly synthesised nucleic acid.

8. The method according to claim 7, wherein said detecting step comprises the use of a molecular beacon or a fluorescent dye, a lateral flow labelled probe, or an enzyme which catalyses an electrochemical reaction.

9. The method according to claim 1, wherein step (b) comprises the use of a nicking enzyme.

10. The method according to claim 1, comprising the use of a first polymerase and/or a first nicking enzyme having an optimum temperature, and a second polymerase and/or a second nicking enzyme having an optimum temperature, wherein the optimum temperature of the second polymerase and/or second nicking enzyme is lower than the optimum temperature of the respective first polymerase and/or first nicking enzyme.

11. The method according to claim 10, wherein the second polymerase is Bsu polymerase or Klenow fragment of DNA polymerase I.

12. The method according to claim 10, wherein the initial temperature of the amplification reaction is at or above the optimum temperature of the first nicking enzyme, and the temperature is reduced during the course of the amplification reaction to a temperature below the optimum temperature of the first nicking enzyme.

13. The method according to claim 12, wherein the temperature of the amplification reaction is reduced to, or below, the optimum temperature of the second polymerase and/or second nicking enzyme.

14. The method according to claim 1, further comprising the step of contacting the mixture obtained by performance of the method with a thermolabile enzyme which degrades nucleic acid, the mixture being contacted with the thermolabile enzyme at a temperature at which the thermolabile enzyme is substantially active.

15. The method according to claim 14, wherein the thermolabile enzyme is cod uracil-DNA Glycosylase (UDG), or Antarctic thermolabile UDG.

16. The method according to claim 1, wherein step (a) is preceded by performing a reverse transcription step, comprising contacting an RNA analyte of interest with a reverse transcriptase so as to form a DNA transcript of the RNA analyte of interest.

17. The method according to claim 16, further comprising the step of making double-stranded DNA from the DNA transcript.

18. The method according to claim 1, further comprising a pre-amplification or enrichment step.

19. The method according to claim 1, wherein one or more of the one or more primers comprises a modified nucleotide.

20. The method according to claim 19, wherein the modified nucleotide is in a target-complementary portion of the primer(s).

21. The method according to claim 20, wherein the one or more primers comprise a 2'-modified nucleotide.

22. The method according to claim 21, wherein the one or more primers comprise a 2'-O-methyl modified nucleotide.

23. The method according to claim 22, wherein the one or more primers comprise a plurality of 2'-O-methyl modified nucleotides.

24. The method according to claim 23, wherein the one or more primers comprise up to seven 2'-O-methyl modified nucleotides.

25. The method according to claim 1, wherein the temperature of the reaction during steps (b)-(d) does not return to the temperature at which step (a) is performed.

26. The method according to claim 1, wherein one or more of the one or more primers comprises a self-complementary portion.

27. The method according to claim 26, wherein the self-complementary portion forms a hairpin structure.

28. The method according to claim 27, wherein the hairpin comprises 5 to 10 base pairs.

29. The method according to claim 1, wherein the magnitude of the temperature reduction during steps (b)-(d) is in the range of 8-20° C.

* * * * *

```
                        SEQUENCE LISTING

<160> NUMBER OF SEQ ID NOS: 6

<210> SEQ ID NO 1
<211> LENGTH: 32
<212> TYPE: DNA
<213> ORGANISM: artificial sequence
<220> FEATURE:
<223> OTHER INFORMATION: primer sequence

<400> SEQUENCE: 1
cgactccata tggagtcgat ttccccgaat ta                               32

<210> SEQ ID NO 2
<211> LENGTH: 32
<212> TYPE: DNA
<213> ORGANISM: artificial sequence
<220> FEATURE:
<223> OTHER INFORMATION: primer sequence

<400> SEQUENCE: 2
ggactccaca cggagtcttt ttccttgttt ac                               32

<210> SEQ ID NO 3
<211> LENGTH: 33
<212> TYPE: DNA
<213> ORGANISM: artificial sequence
<220> FEATURE:
<223> OTHER INFORMATION: primer sequence

<400> SEQUENCE: 3
ccattccttg tttactcgta tttttaggaa tgg                              33

<210> SEQ ID NO 4
<211> LENGTH: 33
<212> TYPE: DNA
<213> ORGANISM: artificial sequence
<220> FEATURE:
<223> OTHER INFORMATION: primer sequence

<400> SEQUENCE: 4
ggactcgata tcgagtccag ttacgatttg ttg                              33

<210> SEQ ID NO 5
<211> LENGTH: 33
<212> TYPE: DNA
<213> ORGANISM: artificial sequence
<220> FEATURE:
<223> OTHER INFORMATION: primer sequence

<400> SEQUENCE: 5
ggactccata tggagtccta cggctccgct ttt                              33

<210> SEQ ID NO 6
<211> LENGTH: 29
<212> TYPE: DNA
<213> ORGANISM: artificial sequence
<220> FEATURE:
```

```
<223> OTHER INFORMATION: primer sequence

<400> SEQUENCE: 6
gctgcgttcc aattcgcctt tttcgcagc                                              29
```